United States Patent [19]
Keller

[11] Patent Number: 5,645,684
[45] Date of Patent: Jul. 8, 1997

[54] MULTILAYER HIGH VERTICAL ASPECT RATIO THIN FILM STRUCTURES

[75] Inventor: Christopher G. Keller, Albany, Calif.

[73] Assignee: The Regents of the University of California, Oakland, Calif.

[21] Appl. No.: 485,815

[22] Filed: Jun. 7, 1995

Related U.S. Application Data

[63] Continuation-in-part of Ser. No. 207,459, Mar. 7, 1994.
[51] Int. Cl.⁶ ............................................. H01L 21/00
[52] U.S. Cl. ........................ 156/643.1; 156/657.1; 216/2; 216/67; 437/228 H; 437/927; 148/33.2; 148/33.4
[58] Field of Search ............... 156/633.1, 636.1, 156/643.1, 645.1, 657.1, 659.11, 662.1; 216/2, 8, 17, 18, 20, 33, 38, 41, 52, 67; 437/228 P, 228 H, 927, 974; 257/247, 248; 148/33.2, 33.4, 33.5

[56] References Cited

U.S. PATENT DOCUMENTS

| | | | |
|---|---|---|---|
| 3,936,329 | 2/1976 | Kendall et al. | 148/187 |
| 3,962,052 | 6/1976 | Abbas et al. | 204/129.3 |
| 4,063,271 | 12/1977 | Bean et al. | 357/49 |
| 4,307,507 | 12/1981 | Gray et al. | 29/580 |
| 4,369,565 | 1/1983 | Muramatsu | 29/580 |
| 4,698,900 | 10/1987 | Esquivel | 437/52 |
| 4,874,484 | 10/1989 | Foell et al. | 204/129.3 |
| 5,126,810 | 6/1992 | Gotou | 357/23.6 |
| 5,131,978 | 7/1992 | O'Neill | 156/653 |
| 5,262,021 | 11/1993 | Lehmann et al. | 204/129.55 |
| 5,271,801 | 12/1993 | Valette | 156/653 |
| 5,296,408 | 3/1994 | Wibarg et al. | 437/927 X |
| 5,399,232 | 3/1995 | Albrecht et al. | 216/2 |
| 5,444,015 | 8/1995 | Aitken et al. | 437/927 X |

FOREIGN PATENT DOCUMENTS 1-138110  5/1989  Japan.

OTHER PUBLICATIONS

W. Lang et al., "Application of Porous Silicon as a Sacrificial Layer," *7th International Conference on Solid–State Sensors and Actuators Digest of Technical Papers*, Jun. 7-10, 1993, pp. 202-205.

*Primary Examiner*—William Powell
*Attorney, Agent, or Firm*—Fish & Richardson, P.C.

[57] ABSTRACT

This invention relates to the area of microelectromechanical systems in which electronic circuits and mechanical devices are integrated on the same silicon chip. The method taught herein allows the fabrication of thin film structures in excess of 150 microns in height using thin film deposition processes. Wafers may be employed as reusable molds for efficient production of such structures. Various material properties may be varied within the structures to produce electrical, mechanical or electromechanical devices.

39 Claims, 25 Drawing Sheets

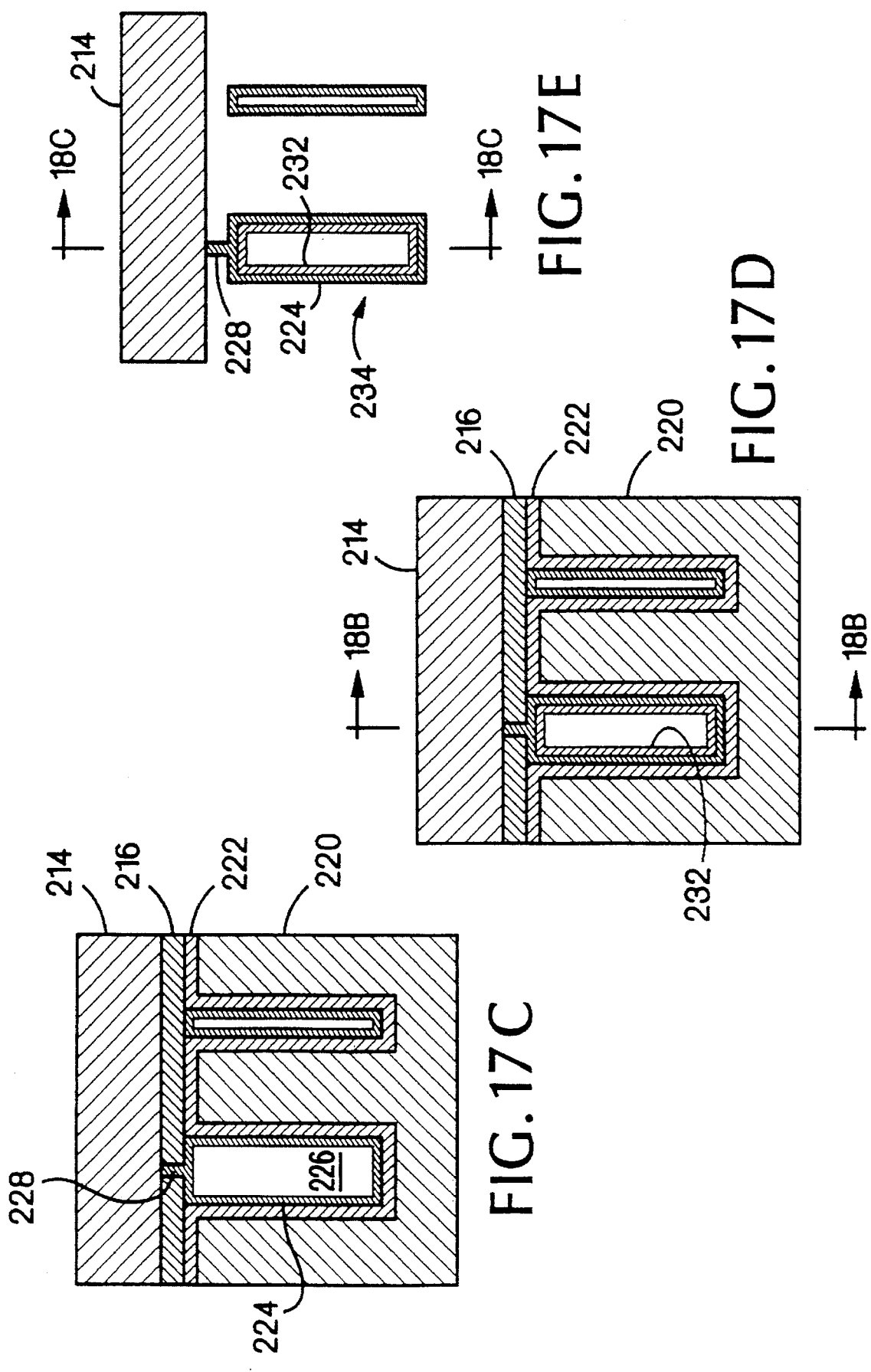

1

MULTILAYER HIGH VERTICAL ASPECT RATIO THIN FILM STRUCTURES

CROSS REFERENCE TO RELATED APPLICATIONS

This application is a continuation-in-part of U.S. patent application Ser. No. 08/207,459, filed Mar. 7, 1994, the entire disclosure of which is incorporated herein by reference.

BACKGROUND OF THE INVENTION

The present invention relates generally to micromachined structures, and more particularly to three-dimensional, thin-film, micromachined structures.

Microelectromechanical systems (MEMS) integrate micromechanical and microelectronic devices on the same silicon chip. These systems have many useful applications such as microsensors and microactuators. The accelerometer chips used to trigger air bag inflation in automobiles in the event of a collision are an example of a microsensor. Microvalves used to control fluidic circuits are an example of microactuators.

Microstructures are made by photolithography and etching of deposited thin films to yield a desired shape. This is called "surface micromachining" because the thin films can only be deposited on a surface. This limits the height of the structure to approximately the thickness of the film. The films are typically formed through the process of chemical vapor deposition (CVD).

Typically, a layer of silicon dioxide is used wherever a sacrificial material is needed. The final step of fabrication is to etch away this material to open up passageways, or clearances between moving parts of the microstructure. Sacrificial layers are needed during processing to prevent structural layers from being deposited directly in contact with already-deposited structural layers, except in locations where interlayer contact and bonding is desired. Since the resulting structures have microscopic thicknesses, they can only withstand microscopic forces without breaking. There has long been a need for a way to make milli-scale structures (structures with dimensions on the order of 100 microns) of any arbitrary shape required. For example, tubing manifolds and enclosed vessels that may be used in fluidic systems such as in the field of microscale chemical processing with liquid or gaseous reagents.

There are methods for making milli-scale structures by chemical etching of silicon wafers, but these are restricted to certain crystal planes and cannot be used to make any arbitrary shape that may be required.

Accordingly, an object of the present invention is to provide free-standing, high-vertical aspect ratio thin film structures.

Another object of the present invention is to provide high-vertical aspect ratio thin film structures integrated with planar electronic circuits.

Yet another aspect of the present invention is to provide free-standing, hollow thin film structures.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention is a thin film structure comprising a network of members shaped as ribs or tubes. The extent of this thin film structure in any direction is greater than about twice the film thickness. A first portion of the structure is composed of a material having certain properties. A second portion of the structure is composed of material having at least one property different from the material composing the first portion of the structure.

The method of the present invention is a method of fabricating of a micromechanical element. A mold having a depth is provided and coated with a sacrificial thin film layer. A first portion of the mold is filled with a material having certain properties. A second portion of the mold is filled with a material having at least one property different from the material filling the first portion of the mold. The sacrificial thin film layer is then etched.

BRIEF DESCRIPTION OF THE DRAWING

The accompanying drawings, which are incorporated in and constitute a part of the specification, schematically illustrate a preferred embodiment of the invention and, together with the general description given above and the detailed description of the preferred embodiment given below, serve to explain the principles of the invention.

FIGS. 17A-17E are schematic, cross-sectional views illustrating steps in the fabrication of the structure of FIG. 19.

DESCRIPTION OF THE PREFERRED EMBODIMENTS

Figure 1:
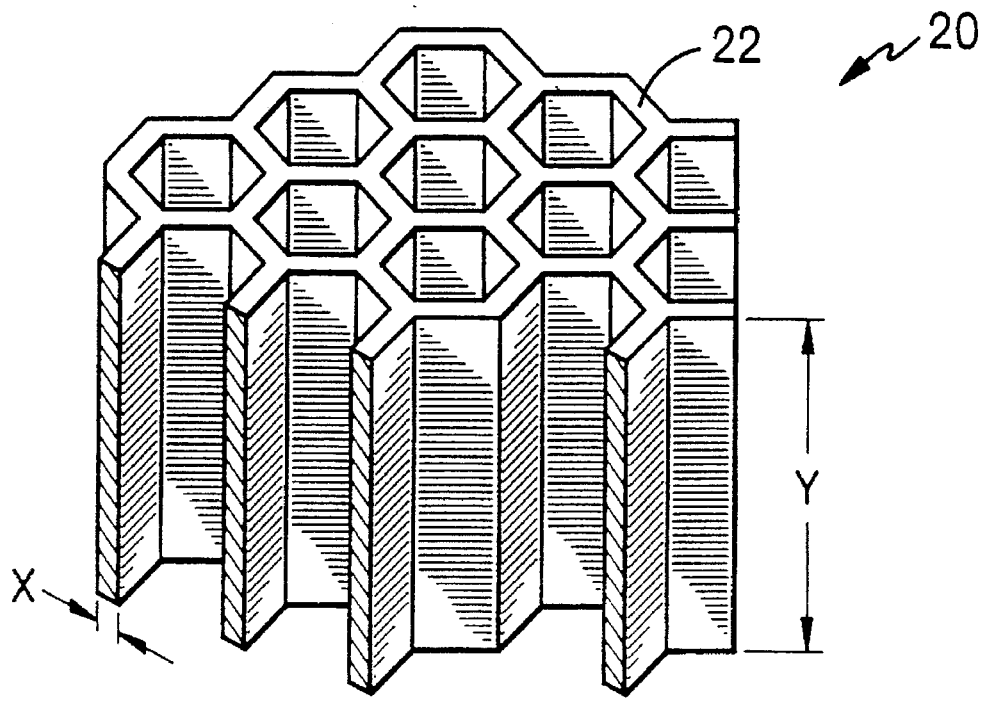
FIG. 1 is a schematic, perspective view of a portion of a high-vertical aspect ratio microelectromechanical structure (HARMEMS) according to the present invention.

The present invention will be described in terms of several preferred embodiments. The preferred embodiments are high vertical aspect ratio thin-film structures or high vertical aspect ratio microelectromechanical structures (HARMEMS) and methods for their fabrication. A portion 20 of such a structure is shown in FIG. 1.

Structure 20 is a honeycomb-shaped network of thin film beams or ribs 22. The thin films forming beams or ribs 22 are oriented in a vertical plane. The vertical extent of structure 20, represented by dimension y, may be in the range of about 5 microns to about 250 microns, with the preferred value being determined by the forces that will be applied to the structure in use, much larger than the thickness of beams 22 represented by dimension x, which may typically be in the range of about 5 microns to about 15 microns. Structure 20 is lightweight, and its mechanical strength is much larger than that of a planar thin film. Since the bending stiffness increases with the cube of the thickness, a 100 micron thick honeycomb is about 125,000 stiffer than the typical 2 micron beams made in the art of surface silicon today. Structure 22 is free-standing and its extent in any direction is greater than twice the thickness of the thin film forming beams 22.

Figure 2:
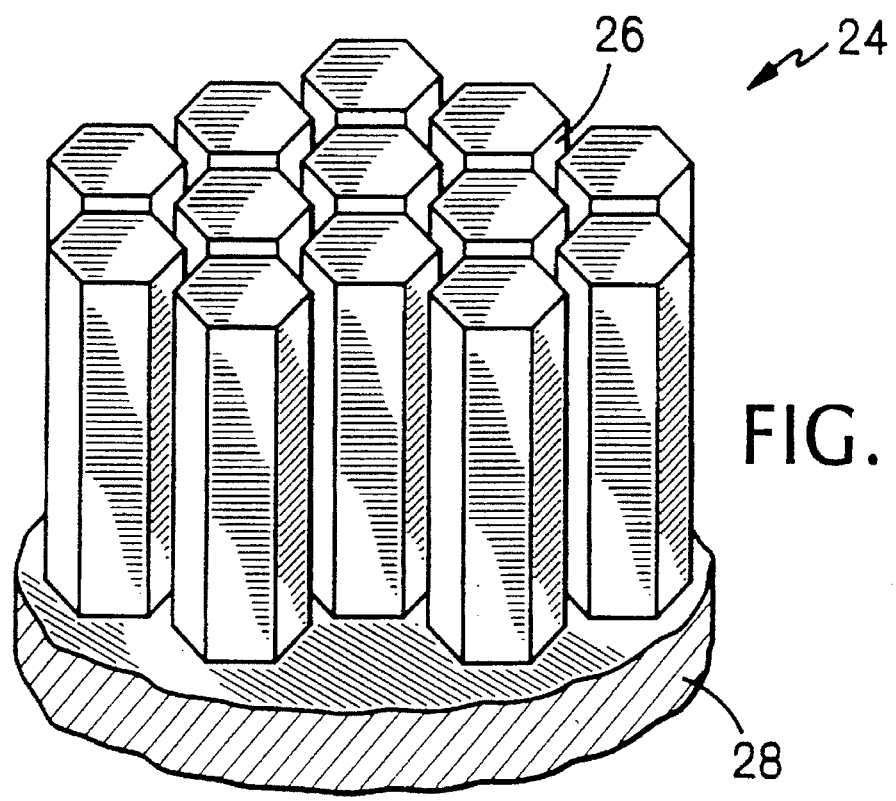
FIG. 2 is a schematic, perspective view of a portion of a mold used to fabricate the structure of FIG. 1.

Structure 20 may be fabricated using mold 24 of FIG. 2. Mold 24 may be formed by anisotropically etching photolithographically patterned vertical trenches 26 in a substrate such as a silicon wafer. The depth of trenches 26 is equal to the desired vertical extent of the HARMEMS 20 to be fabricated. Trenches 26 do not extend all the way through the wafer, leaving an unetched silicon base 28.

To form a silicon mold, a silicon wafer may be coated with sufficient silicon Dioxide to serve as a mask for the required trench etch depth. Silicon dioxide is a good material to use as a mask for etching silicon because it holds up for a relatively long time under the conditions of the silicon etch process. The silicon dioxide may be grown by thermal oxidation of the silicon wafer or by chemical vapor deposition (CVD). The silicon dioxide is coated with photoresist. The photoresist is exposed to a mask which has the desired layout for the HARMEMS. The photoresist is then developed and hardbaked. The pattern is etched to expose the silicon in the areas where the trenches are to be etched. The etch may be done by well known methods, such as wet etching using hydrofluoric acid (HF) or more preferably the oxide mask is etched anisotropically by plasma so that vertical sidewalks are left in the oxide and no significant lateral etching occurs.

The trenches are then etched anisotropically into the depth of the silicon using plasma etching. The parameters for this process may be 180 sccm chlorine, 400 sccm Helium, 300 Watts, 425 millitorr and 0.8 cm gap. The etching plasma is prevented from contacting the silicon that lies under the oxide. This etch step must be terminated before the oxide mask is completely consumed. Typically, the thickness of the oxide decreases by 1 micron during the etching of 20 microns of silicon.

Figure 3A:
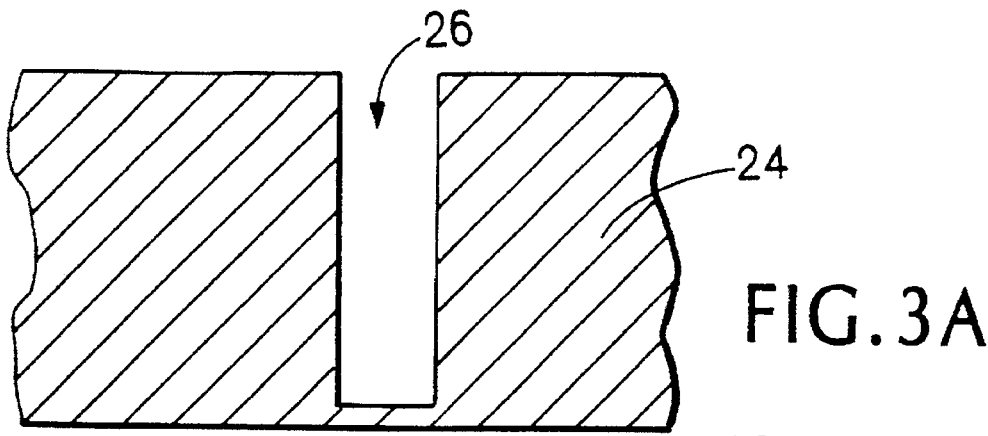
FIGS. 3A–3D are schematic, cross-sectional views of stages in the fabrication of a HARMEMS.

The etched surface of the wafer may be made smoother if desired by growing 1 micron of thermal oxide on it and then etching this oxide away with a solution of 49% hydrofluoric acid (HF). One micron of undoped CVD silicon dioxide (undoped means pure silicon dioxide in this case) may then be deposited. This material is called low temperature oxide (LTO). A cross sectional view of a resulting trench 26 is shown in FIG. 3A. At this point a mold such as mold 24 of FIG. 2 has been obtained.

Figure 3B:
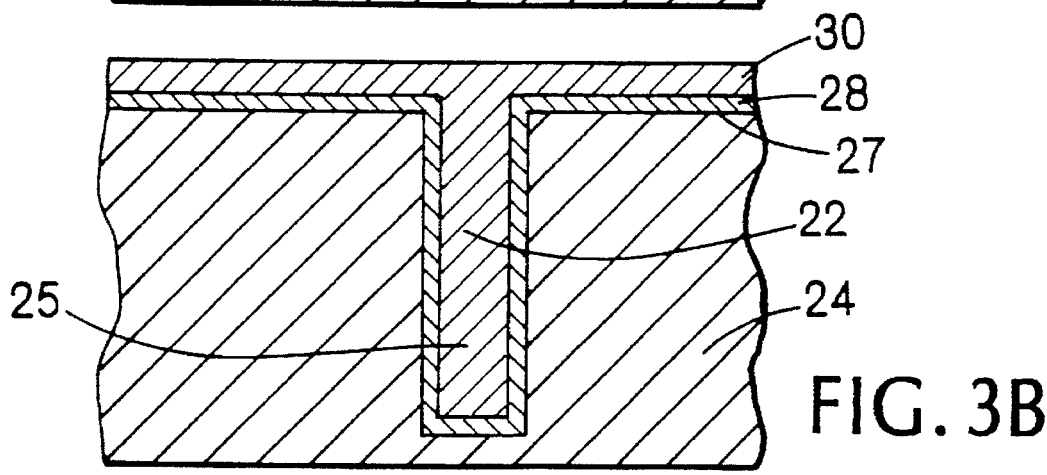

A sacrificial layer 28 is then deposited (FIG. 3B). This layer may consist of up to about four microns of phosphosilicate glass (PSG), that has a high etch rate in HF to facilitate the final removal of the HARMEMS from its mold. The coated mold may be annealed to densify and reflow the PSG to provide a smooth surface. The LTO layer prevents the diffusion of phosphorus into the silicon wafer.

Figure 3C:
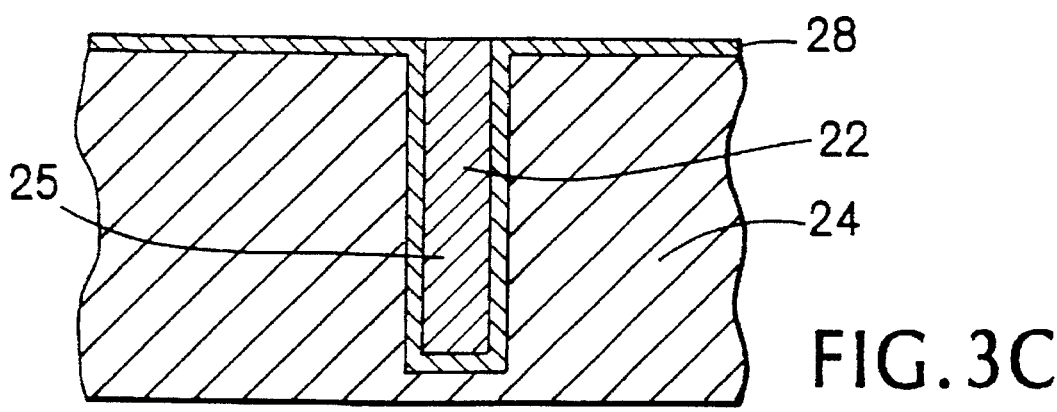

The remaining trench volume is then filled with CVD polysilicon 25. To ensure that the trench is completely filled, the deposition may be done at low temperature such as 580° C. When the trench is completely filled, the structure of FIG. 3B is obtained. Trench 26 and the top surface 27 of mold 24 are coated with a sacrificial layer 28. The remaining trench volume is filled with silicon, forming a beam 22. The thickness of the polysilicon thin film forming beam 22 is less than the depth of mold 24. A layer 30 of polysilicon also covers the mold. Layer 30 was formed at the same time layer 25 was formed. For some applications, such as a reinforced particle filter disclosed in co-pending U.S. patent application Ser. No. 08/207,457, entitled "Microfabricated Particle Filter", filed concurrent with the subject application and assigned to the assignee of the subject application, top layer 30 may be retained as part of the finished device, in which case it may now be patterned photolithographically. If a flat planar surface is desired, the wafer may be lapped and polished, removing part or all of layer 30, as shown by FIG. 3C. The wafer may now be annealed to relieve the internal stresses in the polysilicon, and to diffuse phosphorus from the PSG into the polysilicon to make it conductive. If nonconductive polysilicon is needed, the PSG can be coated with undoped LTO prior to the polysilicon deposition.

Figure 3D:
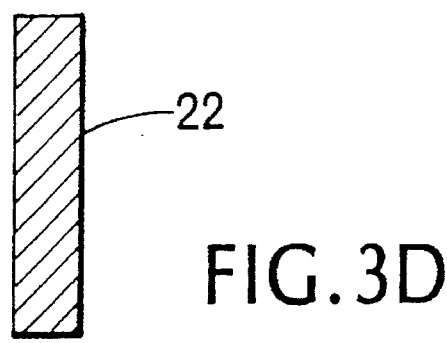

HARMEMS may then be released from the wafer by etching away the sacrificial oxide layer. Beam 22 of FIG. 3D is thus produced.

Surface micromachined microstructures may be built on top of the HARMEMS while it is still held in its mold.

If the trench etching was done under conditions that cause undercutting of the wafer, then hollow beams can be made. These may be used to conduct fluids, or cause movement in response to hydrostatic pressure. Other methods for fabricating hollow structures will be described below.

Figure 4:
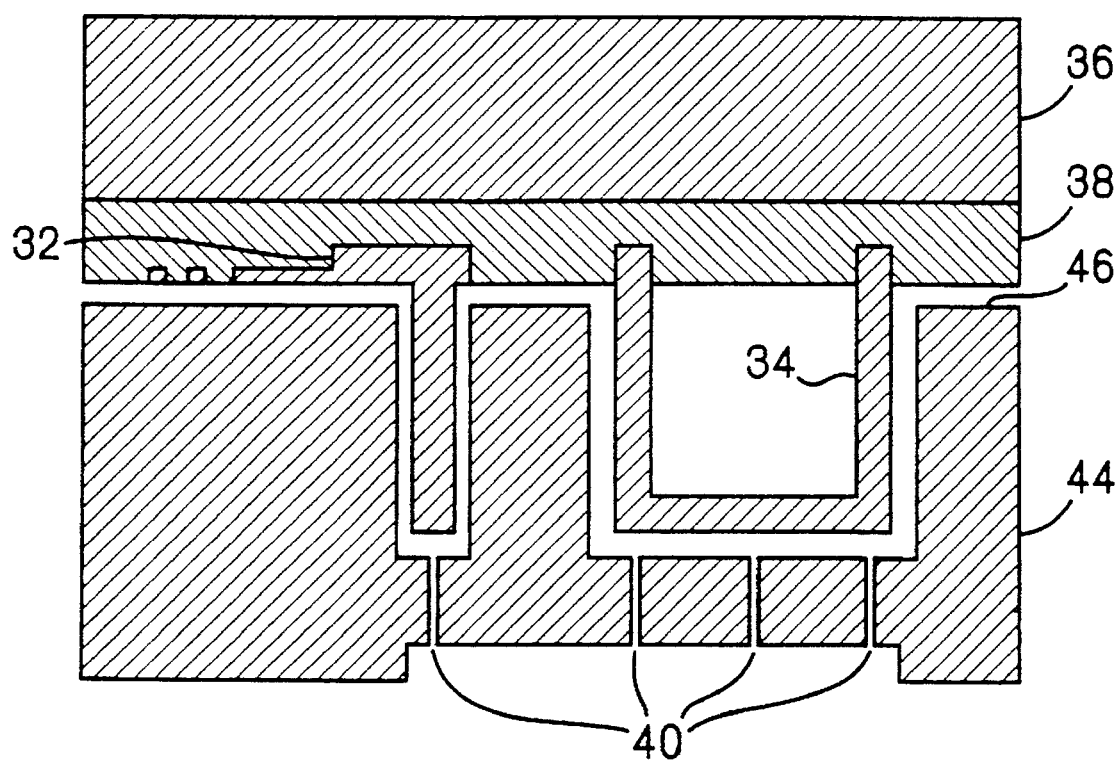
FIG. 4 is a schematic, cross-sectional view illustrating the extraction of HARMEMS from its mold.

FIG. 4 shows the removal of HARMEMS 32 and 34 from their mold 44, after the sacrificial layers coating the mold have been etched. If the wafer was lapped and polished before etching of the sacrificial layers, the HARMEMS extend beyond the top surface 46 of the mold, as shown. A flat wafer 36 with a sticky surface such as a coating of wax 38 may be used to lift structures 32 and 34 from the mold.

If mold 44 is n-type silicon, long small diameter passageways 40 leading to the mold cavities may be photoelectrochemically etched from the back and through the thickness of the mold. Possible process parameters for the electrochemical etching are 10 mA/cm$_2$ etching current, 10% HF concentration, platinum cathode, and light being shined on the back of the wafer i.e. the side opposite the trench patterned side. This technique may be used to connect the bottoms of the mold cavities to a source of hydraulic pressure. The preferred working fluid is deionized water with 0.1% surfactant such as Triton-X100, available from Sigma Chemical Co., 3500 De Kalb, St. Louis, Mo. 63118. To retain the organization of the parts fabricated in mold 44 in accordance with the present invention, the parts can be ejected directly into receiving cavities that have been etched into a second wafer (not shown).

The machines that can be built with the structures of the present invention typically consist of rigid beams connected by flexible links. Rigid structures can be made from thin films by using the thin films to construct a honeycomb structure like the one shown in FIG. 1. The outside perimeter of the honeycomb region, referred generally by reference numeral 55 (FIGS. 5A and 5B), is made in the shape of any desired machine part. This yields a rigid three-dimensional machine part that consists entirely of a relatively thin deposited films. The flexible connecting links in such a structure may be simple single bars of polysilicon, such as links 52 and 58 in FIGS. 5A and 5B.

Figure 5A:
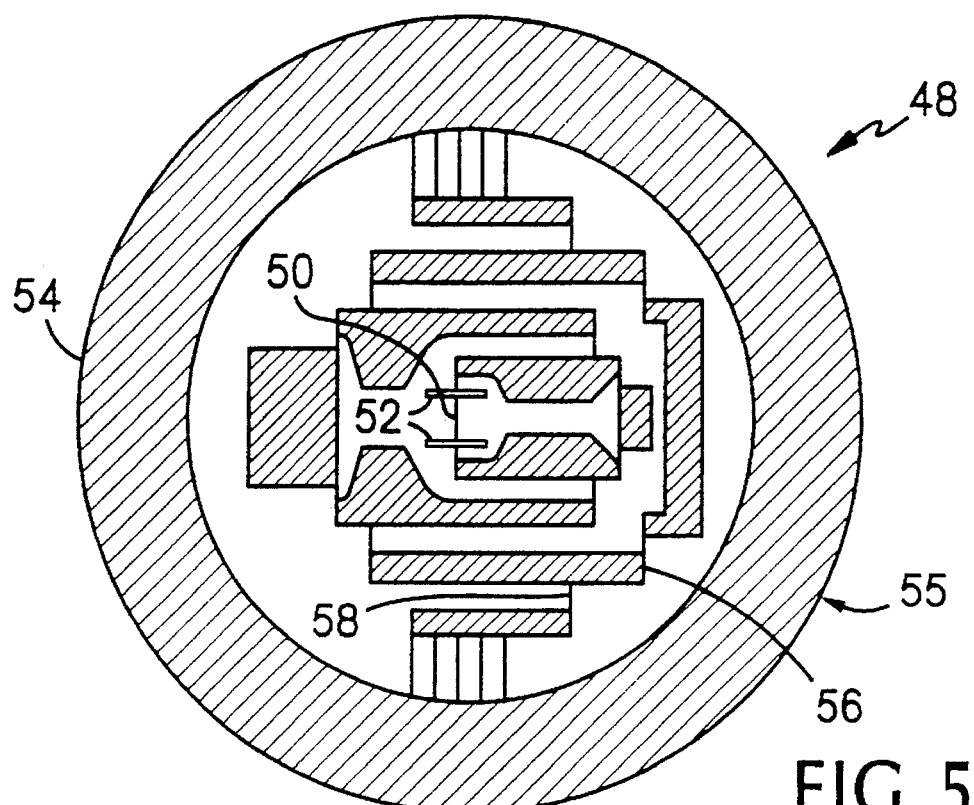
FIGS. 5A–5B are schematic, plan views illustrating the operation of a micro tensile testing machine formed as a HARMEMS.
Figure 5B:
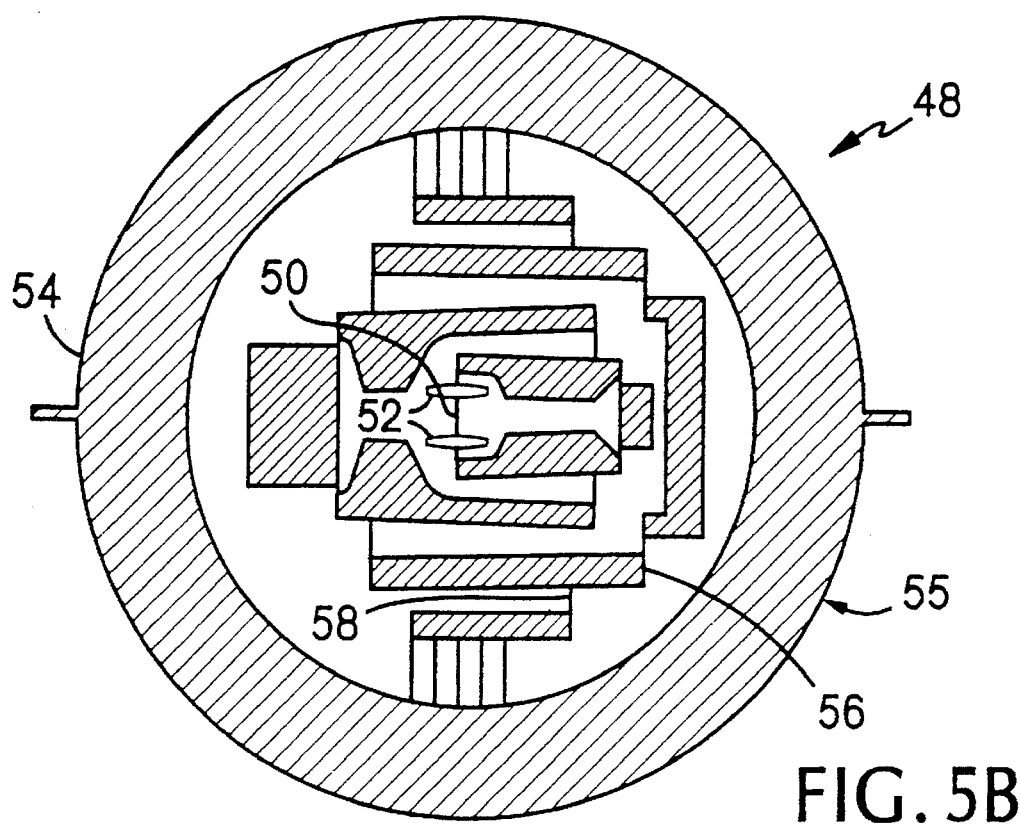

The layout of a microtensile testing machine 48 fabricated as described above is shown in FIGS. 5A and 5B. In these figures, circular frame 54 and member 56 are actually honeycomb structures like that of FIG. 1 whose details are too small to show. The thin lines illustrated in these figures are flexible thin film connecting links, such as link 58 and spring 52. To tension test structure 50, an electric current is passed through frame 54, which as a result heats up and expands. FIG. 5A shows machine 48 at a uniform temperature. In FIG. 5B, frame 54 is at a higher temperature than the rest of the machine. As a result, link 50 is subjected to tensile stress.

Figure 6A:
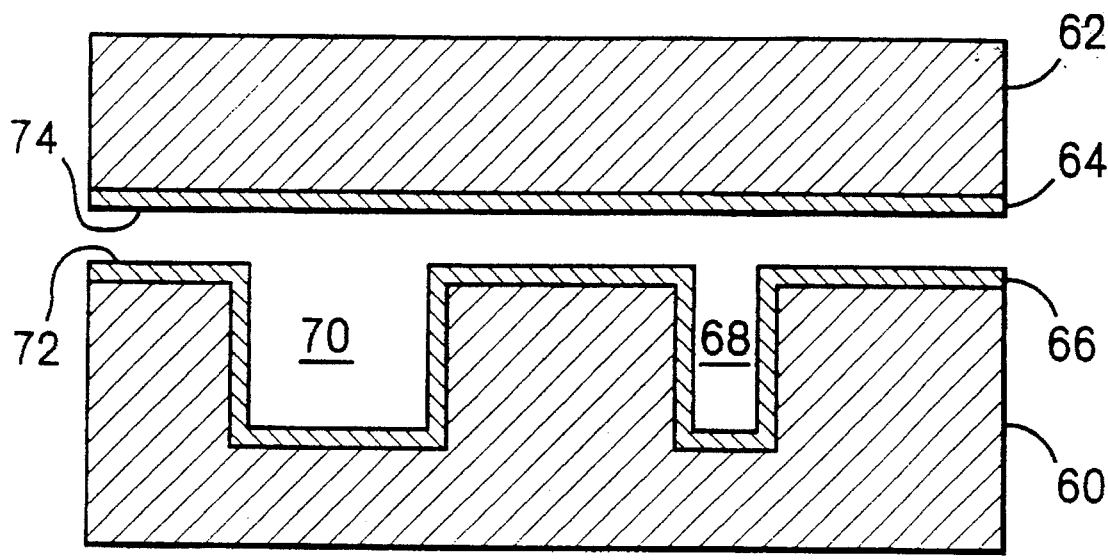
FIGS. 6A–6C are schematic, cross-sectional views illustrating the fabrication of a tubing manifold and a solid HARMEMS.
Figure 6B:
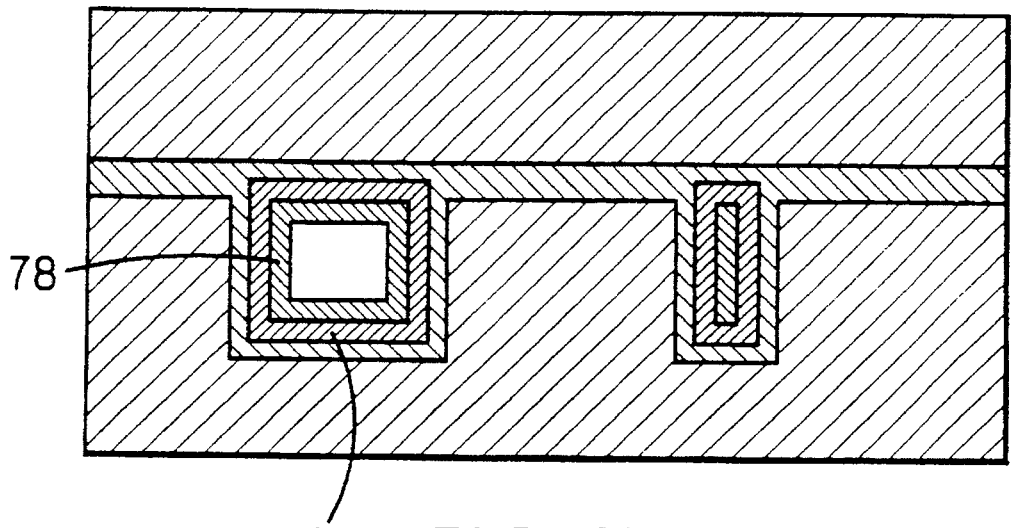

Tubing manifolds may be fabricated by using two wafers to form a mold, such as silicon wafers 60 and 62 of FIG. 6A. Tubing manifolds may be used for controlling fluid flow for microscale chemical reactions. Wafer 60 has mold cavities 68 and 70 etched into it as described above. Wafer 62 is flat. The two wafers are bonded together by anodic bonding, or hydrophilic thermal bonding. For this to work, the contacting surfaces 72 and 74 of the wafers (FIG. 6A) must be extremely flat to ensure a large area of contact. There must be a thin layer of silicon dioxide such as layers 64 and 66, or other easily etchable material, separating the silicon so that the wafer assembly can be taken apart later. Layers 64 and 66 are preferably thermal oxide on the order of 0.5 microns thick. After the wafers are bonded together, a sacrificial layer 76 (FIG. 6B) of PSG is deposited. As discussed, this is a high-etch rate material. If there are any voids left between the bonded wafers where they should be in contact, but where, because of surface imperfections or particle contamination they are not in contact, the PSG will fill such voids as well as line mold cavities 68 and 70. PSG layer 76 may be 1 to 10 microns thick. The PSG is annealed to densify it. This step may be carried out for one hour at 1050° C. A structural layer 78 of low pressure chemical vapor deposition (LPCVD) polysilicon is deposited and then annealed to relieve internal stresses. Structural layer 78 forms the finished parts 80 and 82. The structural layer may be 1 to 3 microns thick, and be annealed for one hour at 1000° C. Thicker polysilicon films can be built up if a stress relief anneal is done after the accumulation of each additional 3 microns of polysilicon. Other CVD films can be used instead of polysilicon. For example, silicon nitride parts can be made.

After the polysilicon deposition and anneal are complete, the polysilicon that has accumulated on the outside of the wafers must be removed to allow the sacrificial oxide layers 76 to be etched. Photoresist is first applied to the wafer to protect the polysilicon at the entry ports to the mold cavities. Small entry ports are simply plugged by photoresist, and in the case of wide entry ports, the photoresist may flow into the mold cavity. There must be no passageway for the etching plasma to strike the polysilicon parts, only the polysilicon film on the exterior of the wafers.

Once the polysilicon has been removed from the outside of the wafer assembly, the sacrificial oxide is exposed and can be etched by HF. An HF solution may be used to etch all of the oxide and PSG since it is a continuous film, even though it has complicated contours due to the presence of the mold cavities. The polysilicon is not etched by HF. It is preferred to cover the etching chamber with an opaque layer (such as aluminum foil) because photons can cause n-type silicon to etch.

Figure 6C:

Once the sacrificial material is dissolved, the wafers can be separated and the parts can be removed. The finished parts 80 and 82 are shown in FIG. 6C.

Figure 7B:
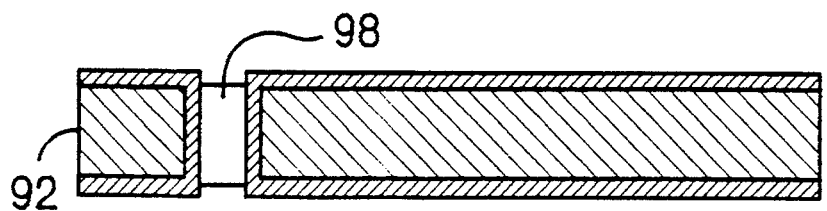
FIGS. 7B–7E are schematic, cross-sectional views illustrating the fabrication of the enclosed vessel of FIG. 7A.
Figure 7C:
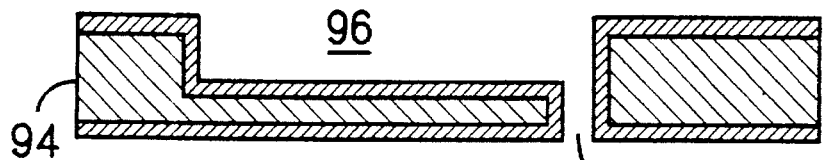
Figure 7C:
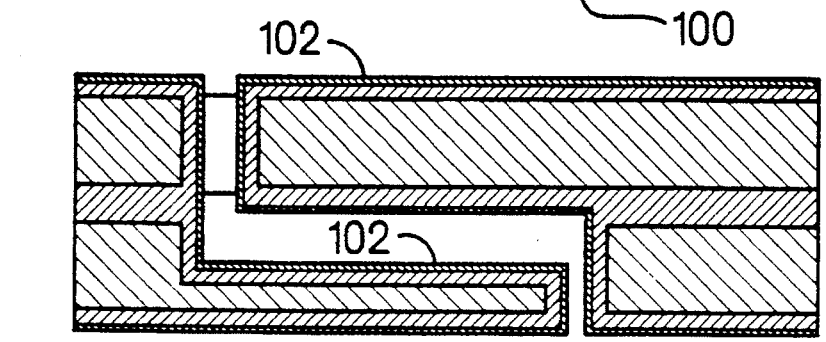
Figure 7D:
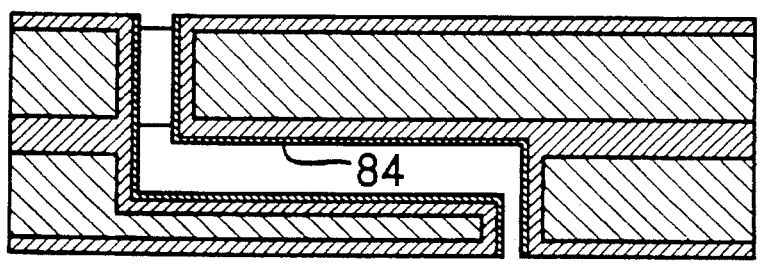
Figure 7E:
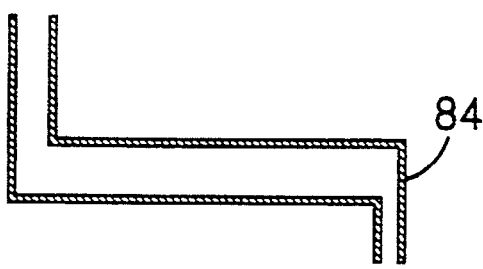
Figure 7A:
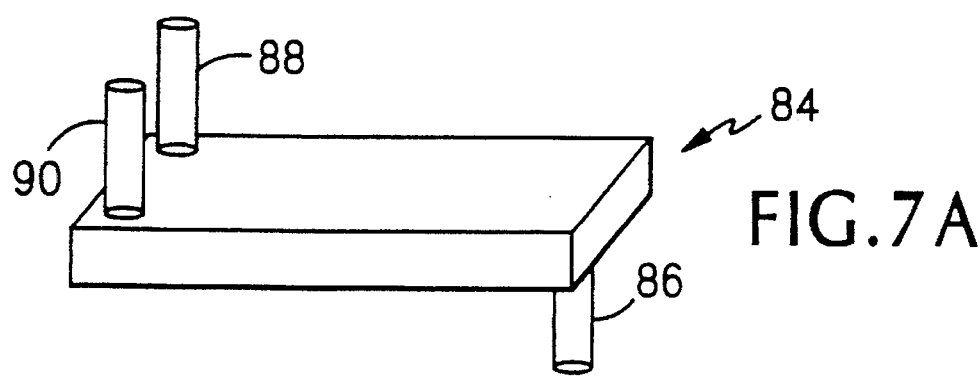
FIG. 7A is a schematic, perspective view of an enclosed vessel with ports according to the present invention.

The same process may be used to make enclosed vessels with ports, such as vessel 84 of FIG. 7A, with ports 86, 88 and 90. Such vessels may be used for fluidic devices such as microactuator 104 of FIGS. 8A and 8B. The size of the vessels may be, for example, about 5 microns×5 microns× 100 microns. The ports are formed by providing passages from the mold cavity used to form the body of the vessel to the outside of the mold. The molds 92 and 94 used to fabricate vessel 84 are shown in cross-section in FIG. 7B. The body of vessel 84 is formed using cavity 96 of mold 94. Port 86 is formed using passage 100 of mold 94. Ports 88 and 90 are formed using passage 98 of mold 92 and an additional passage (not shown) of mold 92. The passages may be fabricated using photoelectrochemical etching. Molds 92 and 94 are bonded and coated with a sacrificial layer of silicon dioxide as discussed above in the case of the tubing manifold fabrication. A structural layer 102 of polysilicon is then applied and annealed, as discussed above and shown in FIG. 7C. The polysilicon 102 on the outside of the mold is removed as discussed above and shown in FIG. 7D, leaving behind the polysilicon structure of vessel 84. The vessel is then freed, as shown in FIG. 7E, by etching the sacrificial layer coating the mold.

Figure 8A:
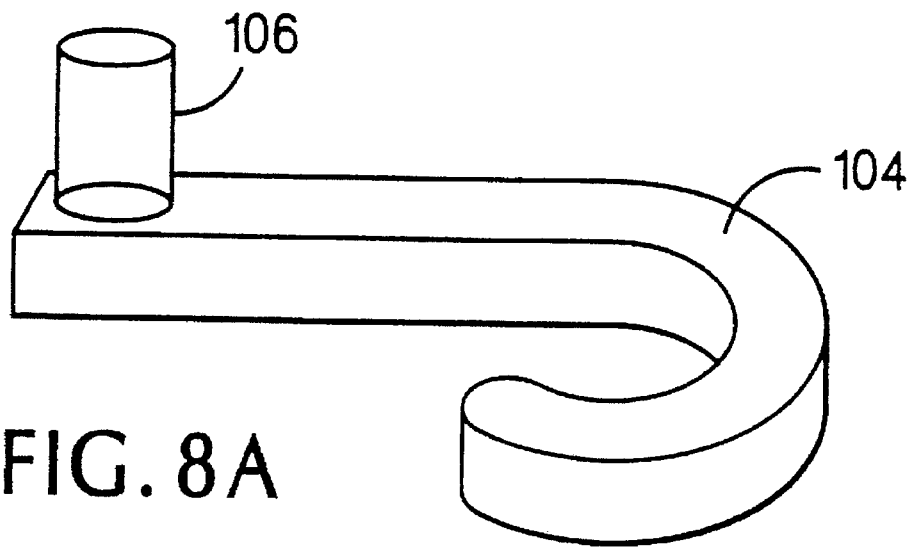
FIGS. 8A and 8B are schematic, perspective views of a hydrostatic actuator or ambient pressure gauge according to the present invention, subject to different pressures.
Figure 8B:
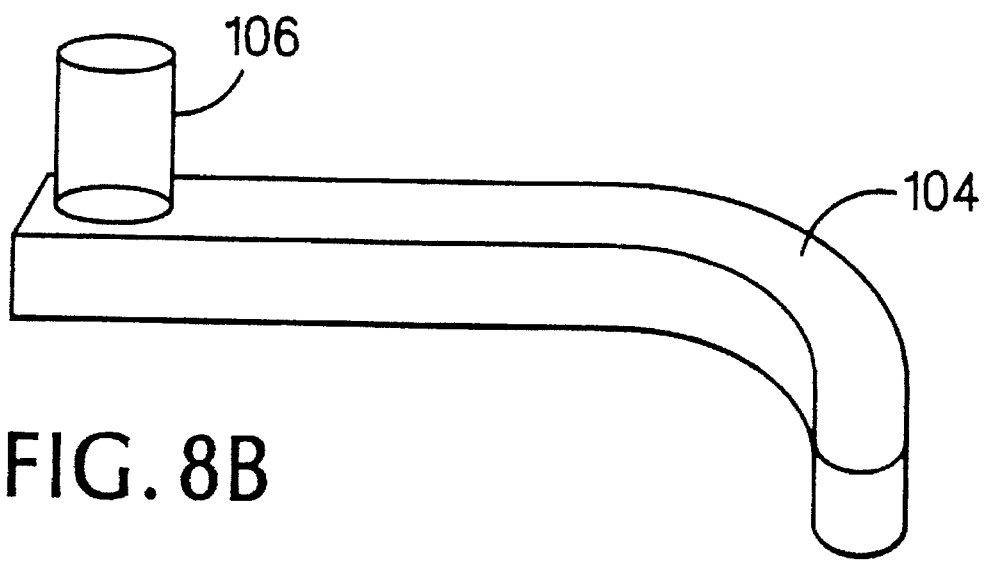

The curved enclosed vessel 104 with one port 106 of FIG. 8A may be used as a hydrostatic actuator or as a Bourdon pressure gauge. When the internal pressure is greater than the external pressure, the curved tube tends to straighten out, as shown in FIG. 8B.

HARMEMS may be integrated with surface silicon applied to the surface of the wafer used as the HARMEMS mold. The term "surface silicon" refers to silicon structures that have a thickness (perpendicular to the wafer they were formed on) on the order of 2 to 6 microns. The resulting structure is a silicon on insulator (SOI) structure. SOI is a silicon wafer on which a layer of silicon dioxide has been formed (typically 1 to several microns thick), and then a second silicon wafer is bonded to this oxide surface. The second wafer is lapped down and polished to leave just a thin layer of single-crystal very large scale integration (VLSI)-quality silicon on the order of 1 to several microns thick, depending on the application. The present invention makes it possible to build an SOI wafer using a HARMEMS mold wafer as the foundation, and then to anchor regions of the SOI wafer to the buried HARMEMS. After the final etch release step, this yields a micromachine carrying microcircuits, unencumbered by a silicon die. This is useful for applications where volume and mass must be minimized.

Figure 9A:
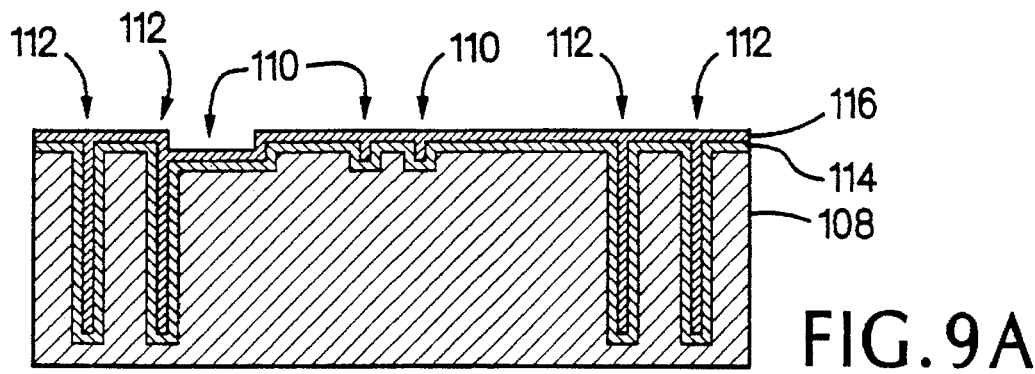
FIGS. 9A–9E are schematic, cross-sectional views illustrating the fabrication of a silicon on insulator (SOI) structure with HARMEMS and surface silicon.

Fabrication of the mold wafer used as the SOI foundation begins with the etching of an alignment pattern on the back of the wafer. This alignment pattern will be used as a reference on a double sided alignment machine for placing the patterns of later mask layers in precise registration with each other. Two microns of LTO are then deposited on the wafer and densified by annealing for 1 hour at 1050° C. The LTO is patterned to provide the etch mask for the surface silicon structures. The silicon of the wafer is plasma etched to a depth equal to the desired thickness of the surface silicon structures plus the thickness of the sacrificial oxide. FIG. 9A shows a wafer 108 with recesses 110 provided as described above.

Trenches 112 (FIG. 9A) for the HARMEMS are fabricated next. Four microns of LTO are deposited and densified as described above. The LTO is patterned to provide a mask for etching the HARMEMS mold trenches 112. The silicon wafer is plasma etched to the depth of the desired HARMEMS plus the desired sacrificial oxide. All the oxide is then removed by HF. As previously described, the wafer may optionally be thermally oxidized and the oxide removed by HF to smoothen the surfaces produced by etching. At this point, the mold wafer is finished, with the final shape shown in FIG. 9A for wafer 108.

A sacrificial PSG layer 114 (FIG. 9A) is then deposited and densified. Next, the structural layer 116 of amorphous LPCVD silicon is deposited and annealed. The wafer is lapped and polished back to the original silicon surface. It is like a new wafer, except that it has mechanical structures buried in it.

Figure 9B:
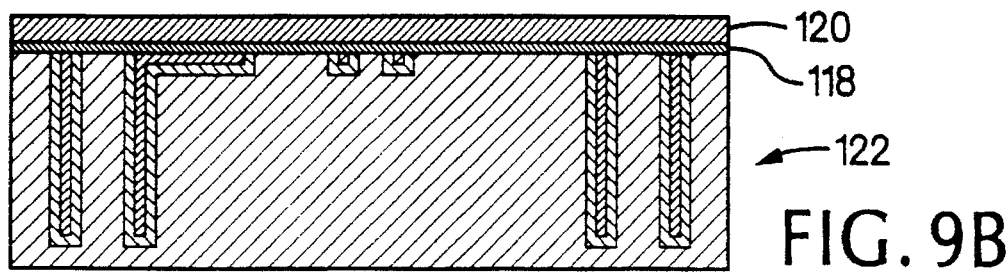

A layer of LPCVD silicon is next deposited and thermally oxidized to yield a layer of silicon dioxide 118 (FIG. 9B). A second silicon wafer (not shown) is bonded to the silicon dioxide surface. This second wafer is lapped and polished down to the desired final thickness for the electronic silicon layer 120. The resulting wafer 122 now looks exactly like a standard SOI wafer and can be processed as such.

Figure 9C:
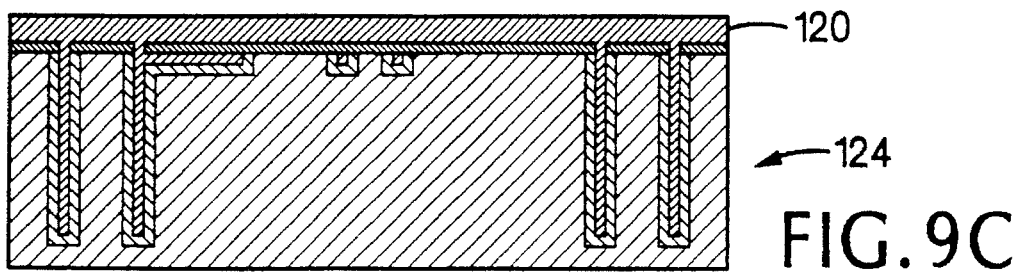
Figure 9D:
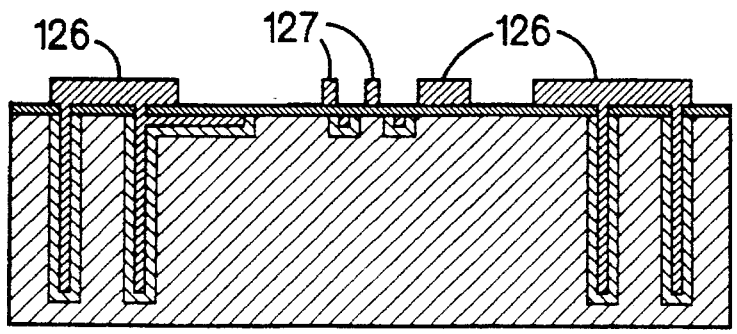
Figure 9E:
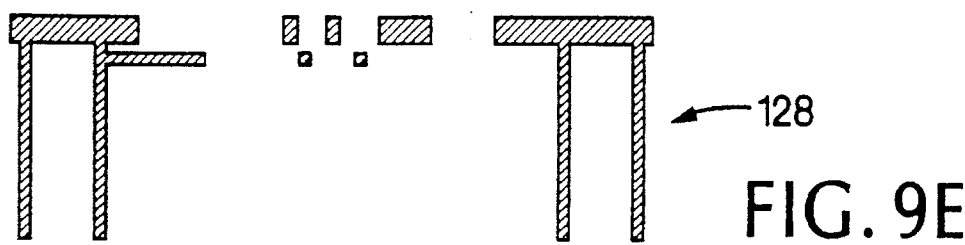

Using the alignment pattern on the back of wafer 122 as a reference, a pattern for anchor contact holes is photolithographically placed on the SOI layer 120. The contact holes are above the buried silicon structures. In the embodiment illustrated in FIGS. 9A-9E, the contact holes would be above trenches 112. The contact holes are etched through the SOI layer and then the oxide layer to expose the surface of the polysilicon of the buried HARMEMS. LPCVD polysilicon is then deposited to fill the contact holes and bond the SOI layer to the buried silicon structures. The surface layer of polysilicon is lapped and polished to leave only the polysilicon in the contact holes and expose the surface of SOI layer 120. The resulting structure 124 is shown in FIG. 9C.

Standard VLSI processing may now be used to fabricate electronic devices in the SOI layer.

The SOI layer 120 is patterned and etched to leave only islands 126 (FIG. 9D) that are located in the desired places on the mechanical structures, including flexible (by virtue of sinusoidal shape) doped conducting interconnects for carrying current between islands 126. The electronic devices (not shown) are covered with a standard silicon nitride passivation layer (not shown), so they are protected from this and subsequent etching processes. The patterning of the SOI layer may also provide a layer of surface silicon type mechanical structures 127 which may interact in cooperation with the surface structures of the polysilicon layer. The completed machine 128 (FIG. 9E) can now be released from the wafer and removed by etching sacrificial layers 114 and 118 as described above.

Figure 10:
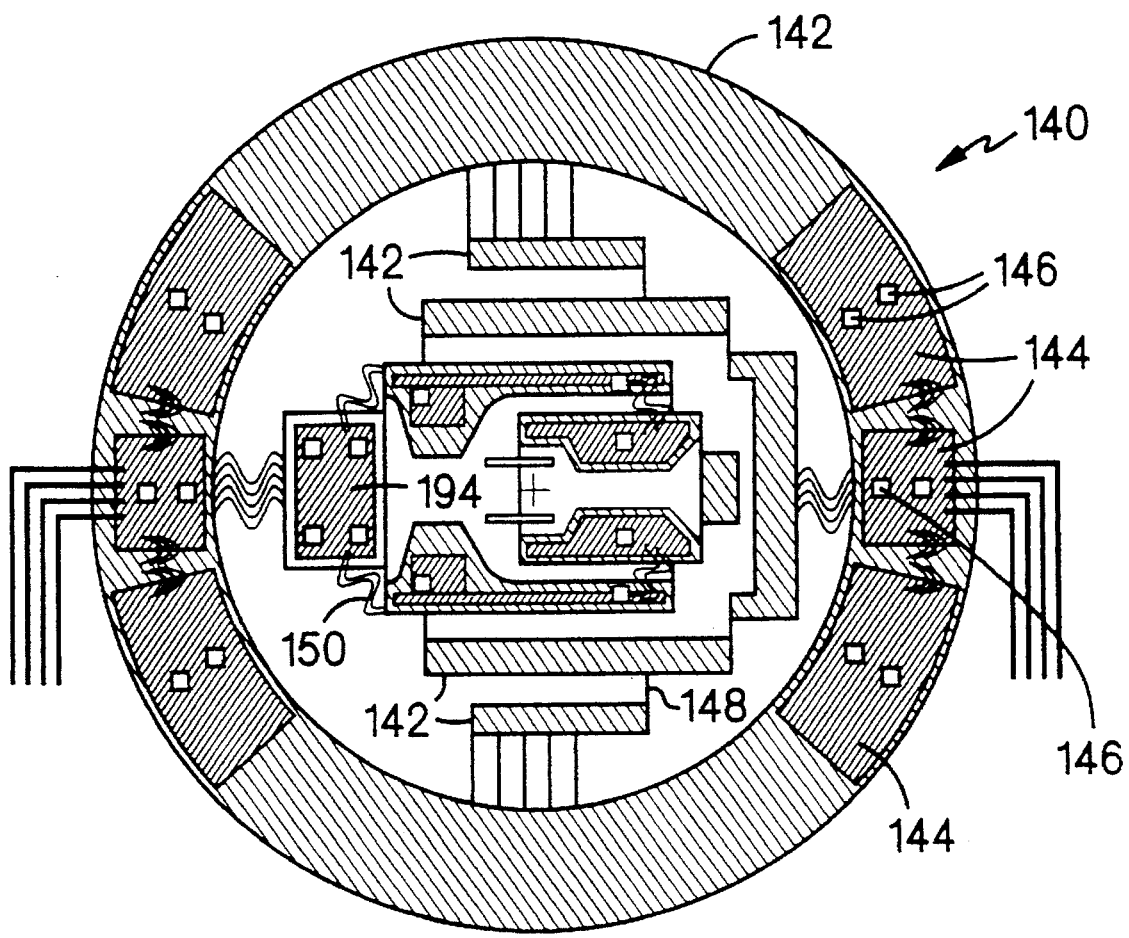
FIG. 10 is a plan view of a machine fabricated using the process of FIGS. 9A–9E.

The design of a machine 140 fabricated using the above process is shown in FIG. 10. The rigid mechanical structures 142 are made of HARMEMS. Overlying some of these structures are layers of single crystal silicon 144, anchored onto the HARMEMS with polysilicon anchors 146. The machine also comprises flexible polysilicon beams 148 and silicon interconnects 150.

Figure 11A:
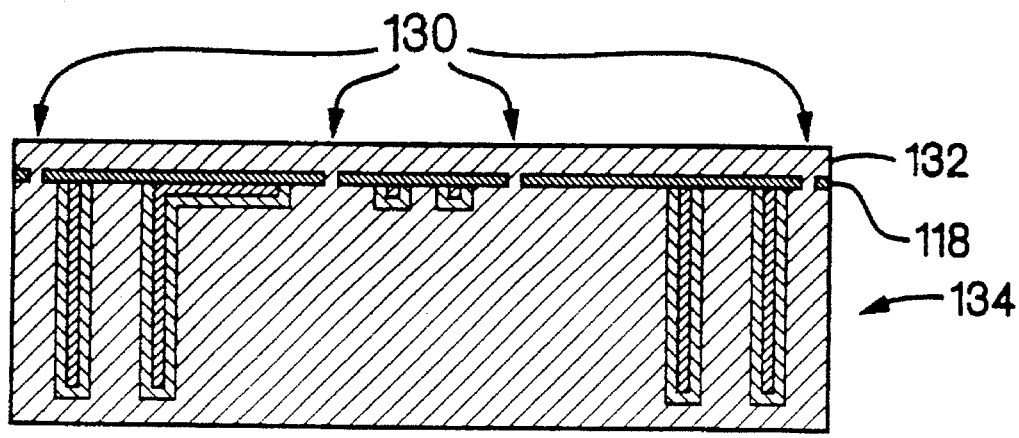
FIGS. 11A and 11B are schematic, cross-sectional views illustrating steps in the fabrication of a SOI structure with HARMEMS and thin film transistor quality recrystallized silicon.
Figure 11B:
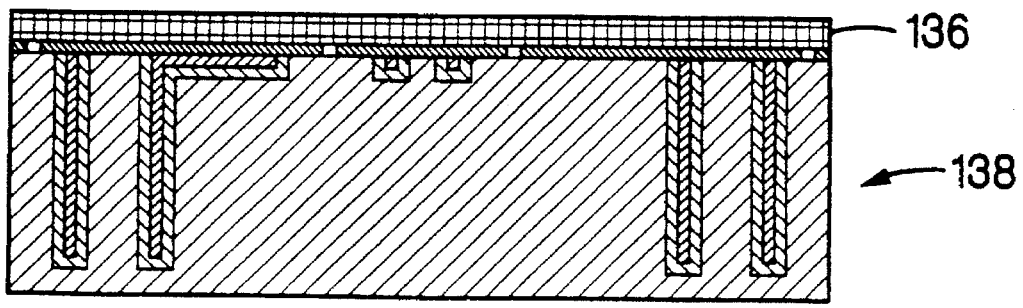

In cases where low performance electronics is adequate, the electronic circuitry layer may be made as described above, but instead of using the SOI strategy to provide VLSI quality silicon, thin film transistor (TFT) quality silicon can be used. As shown in FIG. 10A, the processing sequence is similar to the SOI construction up to the point where the thermal oxide layer 118 is formed. Next, recrystallization windows 130 are etched through layer 118 to expose the surface of the single crystal silicon wafer. LPCVD layer 132 of amorphous polysilicon is deposited next, resulting in the structure 134 of FIG. 11A. The wafer is then annealed at about 600° C. in a recrystallization furnace. The regions of the amorphous silicon 132 that are in contact with the single crystal wafer surface proceed to nucleate the crystallization process, thereby propagating the existing silicon crystal lattice arrangement from the wafer surface up and laterally throughout the LPCVD silicon film. The resulting recrystallized silicon film 136 (FIG. 11B) has too many defects for VLSI circuitry, but it is adequate for many small scale integration (SSI) applications. The resulting structure 138 is similar to structure 122 of FIG. 9B. The subsequent steps are similar to the ones described above for the SOI device case.

Figure 12A:
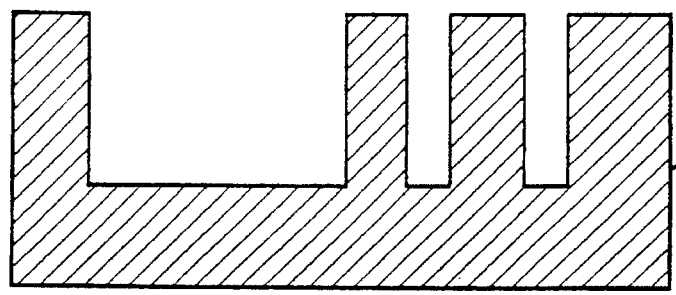
FIGS. 12A–12E are schematic, cross-sectional views illustrating steps in the fabrication of micromechanical structures with very high vertical aspect ratios.
Figure 12B:
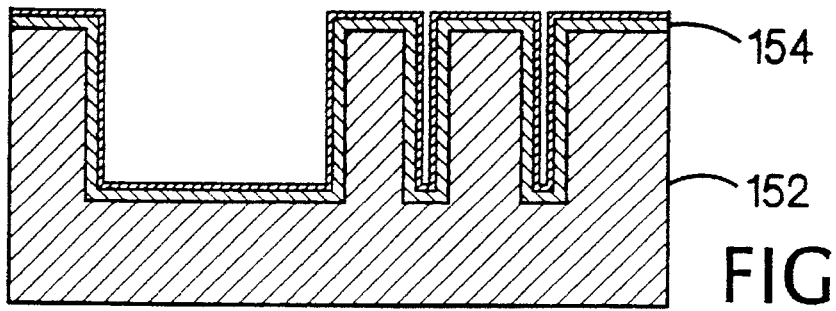
Figure 12C:
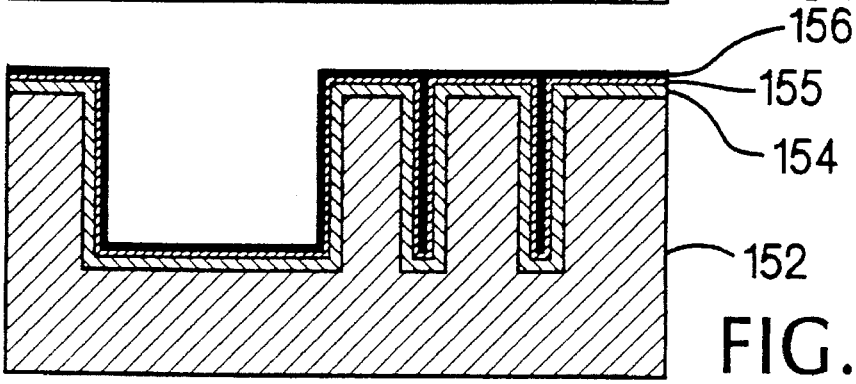
Figure 12D:
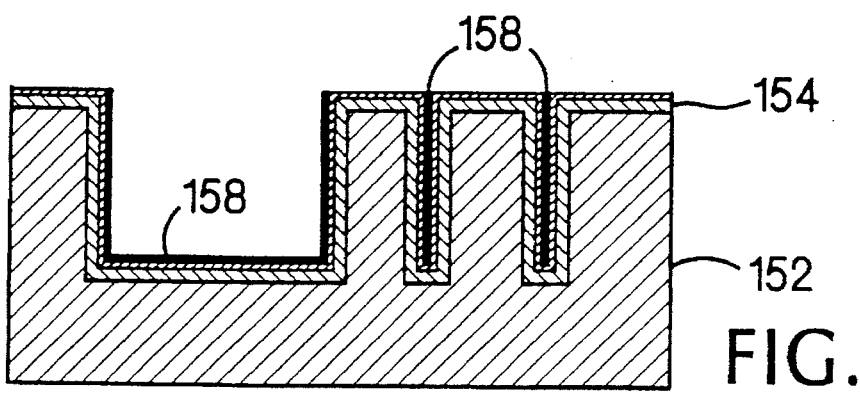
Figure 12E:
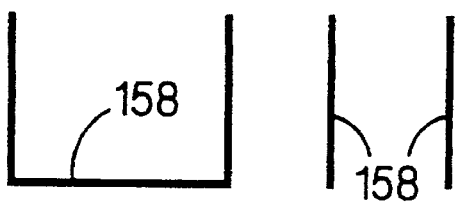

The vertical aspect ratio attainable with anisotropic etching of silicon and PSG sacrificial layers is limited by the unevenness of the PSG layer. Higher vertical aspect ratio structures may be fabricated using a method described with reference to FIGS. 12A-12E. A mold 152 is fabricated as described above. The mold is coated with a layer 154 of CVD polysilicon (FIG. 12B), whose thickness is more constant than that of PSG. Polysilicon 154 is thermally oxidized to obtain a sacrificial layer 155 (FIG. 12C). From this point on, the process is the same as previously described. A structural layer 156 of polysilicon is deposited (FIG. 12C), the surface layer is lapped off (FIG. 12D), and then the polysilicon structures 158 (FIGS. 12D, 12E) are released.

Figure 13:
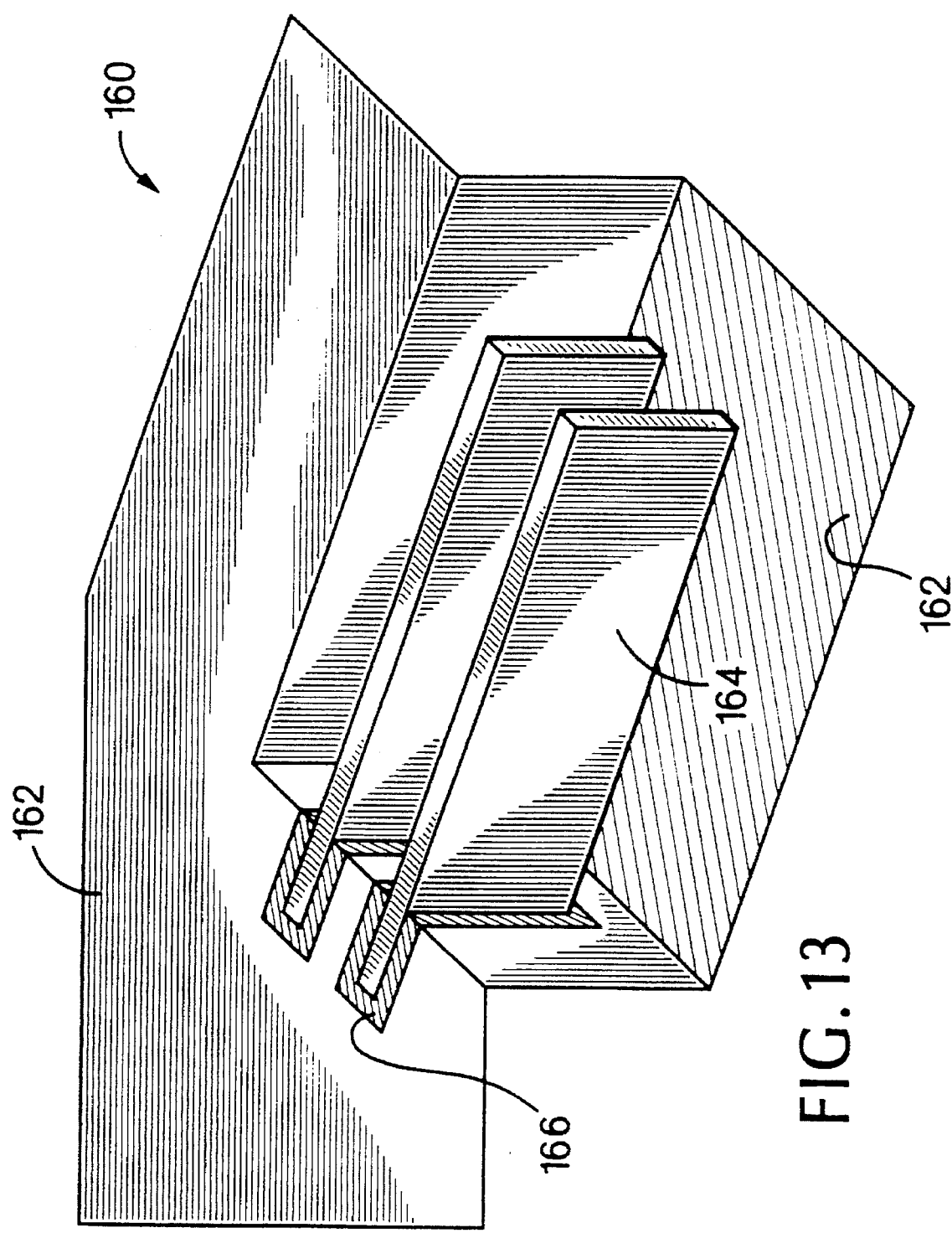
FIG. 13 is a perspective, schematic view of two cantilever beams with large mechanical clearance to wafer.
Figure 14A:
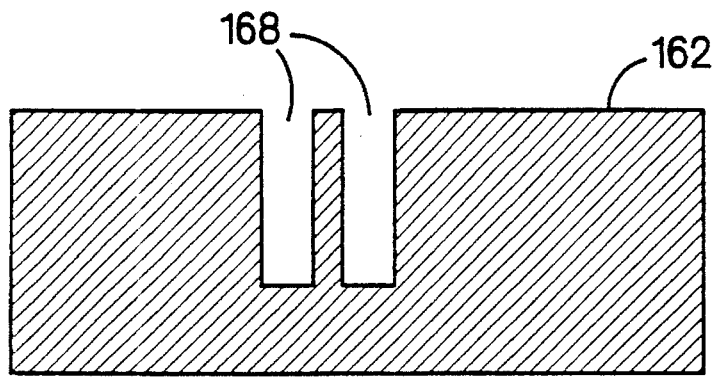
FIGS. 14A–14H are schematic, cross-sectional views illustrating steps in the fabrication of the structure of FIG. 13.
Figure 14B:
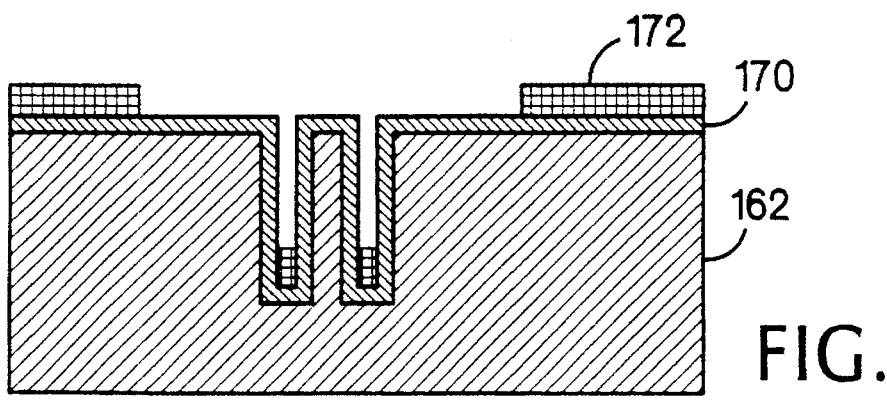
Figure 14C:
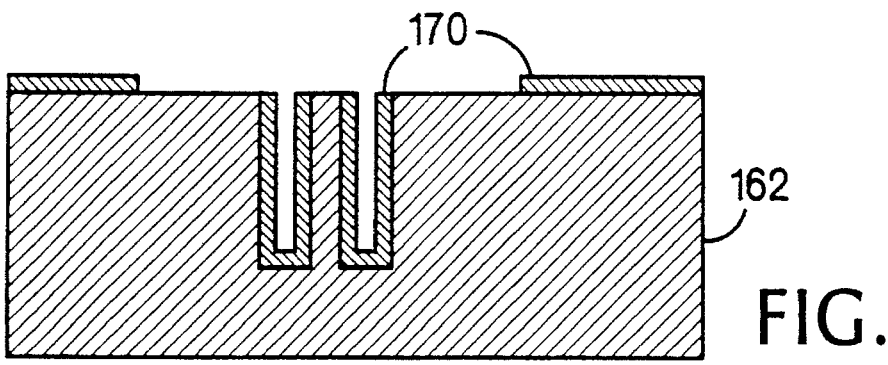
Figure 14D:
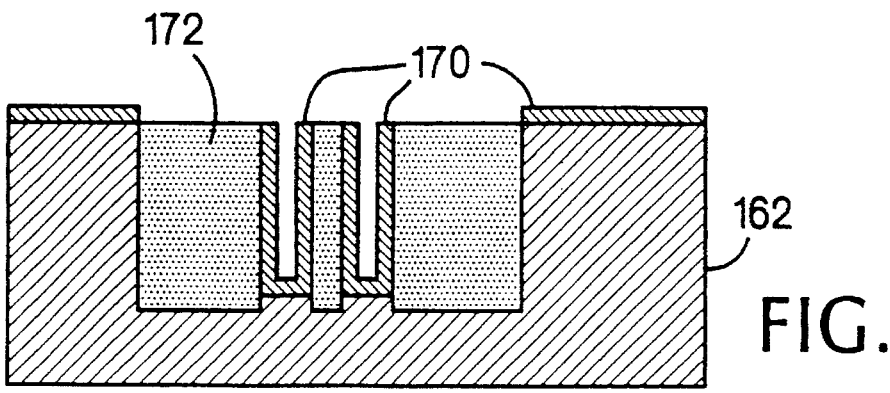
Figure 14E:
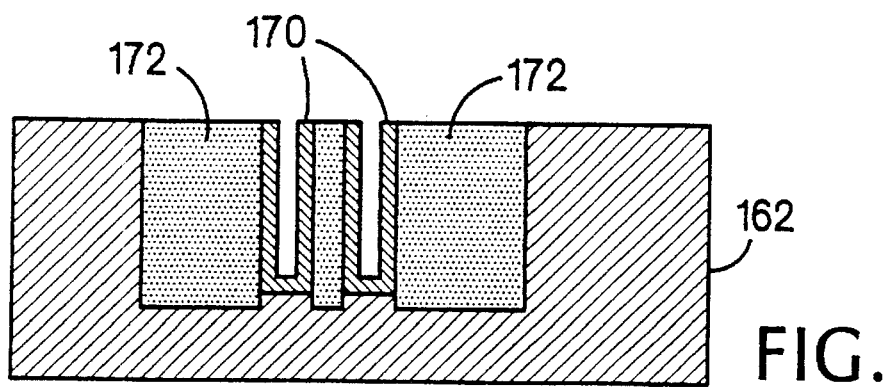
Figure 14F:
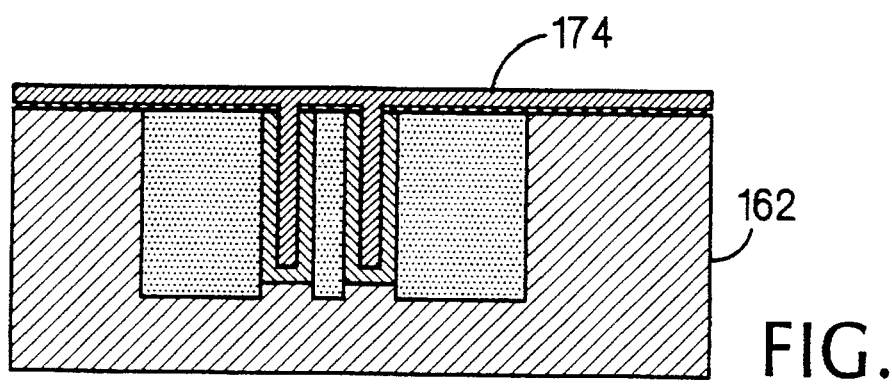
Figure 14G:
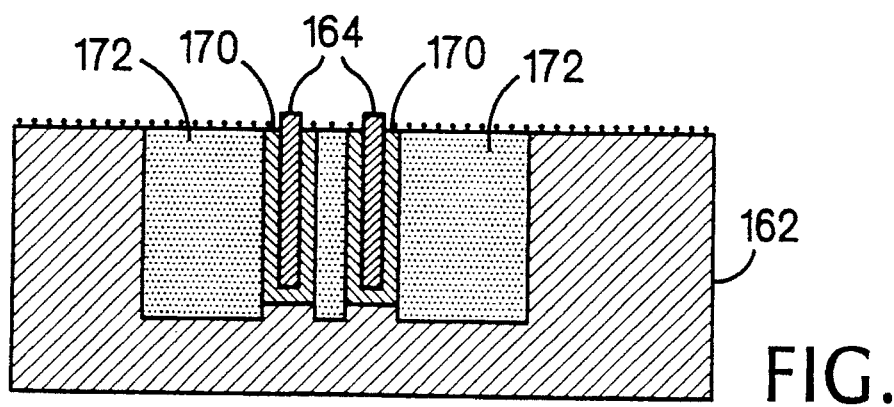
Figure 14H:
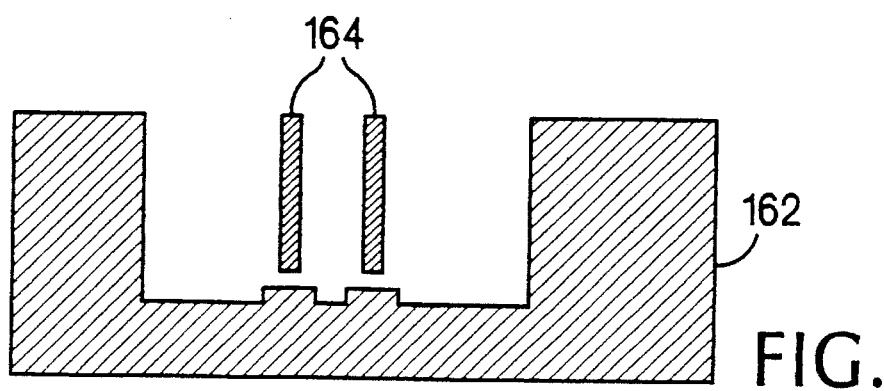

It is also possible to fabricate HARMEMS structures permanently bonded to a wafer and with large final clearance to the wafer. Such a structure 160 is shown in FIG. 13. The structure comprises a substrate 162 and beams 164 anchored to the substrate by anchors 166. Such a structure may be fabricated as described with reference to FIGS. 14A-14D. As shown in FIG. 14A, wafer 162 is first patterned with trenches 168 that serve as molds for the HARMEMS. A bilayer 170 of silicon nitride and polysilicon is then deposited, to serve as a mask for the andization step to follow and as anchors 166. As shown in FIG. 14B, bilayer 170 is patterned using photoresist 172. The bilayer is then etched anisotropically, using C12 for the polysilicon and $CF_4$ and $HCF_3$ for the silicon nitride. The resulting structure is shown in FIG. 14C. The silicon wafer 168 is then anodized and the resulting porous silicon oxidized to obtain the structure of FIG. 14D containing silicon dioxide 172. As shown in FIG. 14E, the top portion of bilayer 170 is then removed, for example by lapping and polishing. A structural layer of polysilicon 174 is deposited as shown in FIG. 14F. Its top layer is removed as shown in FIG. 14G. Finally, oxide 172 and bilayer 170 are removed using HF. Anchors 166 (FIG. 13) are masked by the silicon of wafer 162 and not significantly etched.

HARMEMS structures composed of multiple materials may also be fabricated, as disclosed below. Such combinations of materials may be used to control the mechanical or the electrical properties of the devices.

In order to increase the toughness of the structures, their material may be fiber reinforced. FIGS. 15A–15E show a method for fabrication of tungsten fiber-reinforced polysilicon structures. As described above, fabrication begins with a mold wafer 176 with a trench 178 etched in it. The etching may be done by dry etching with a mixture of chlorine (180 sccm) and helium (200 sccm) at a pressure of 425 millitorr (mT), and an electrode gap of 0.8 cm to provide an etch rate of 1 micron/minute. After every 30 minutes the wafer should be put in isotropic Si wet etch (1890 ml concentrated nitric acid, 960 ml deionized water and 75 ml 40% aqueous ammonium fluoride) for about two minutes to remove sidewall deposits, and after the final plasma etch the wafer should be put in the above-described wet etch for 15 minutes to smooth the trench surfaces. Silicon dioxide used as an etch mask provides a selectivity of 20:1. A sacrificial oxide layer 180 is then deposited over the surface. This layer may be deposited by chemical vapor deposition (CVD) at a temperature of 450° C. and pressure of 300 mT, with a gas flow of 90 sccm oxygen and 60 sccm silane.

Figure 15A:
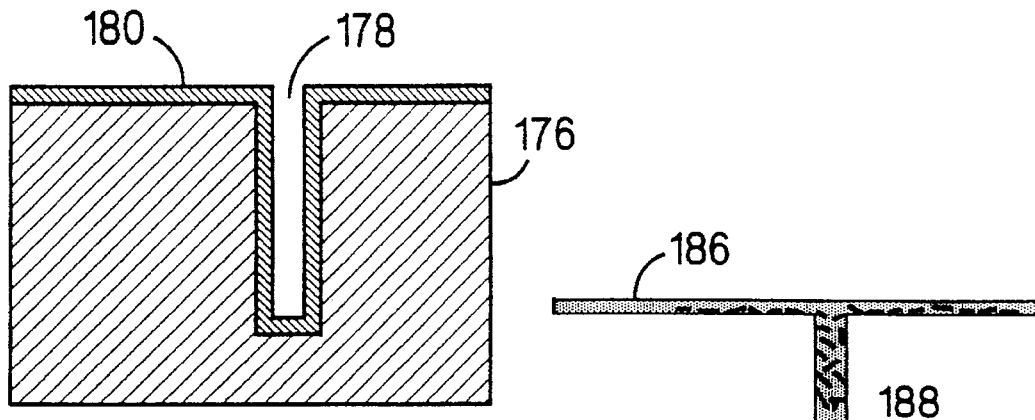
FIGS. 15A–15E are schematic, cross-sectional views illustrating steps in the fabrication of a fiber-reinforced thin film structure.
Figure 15D:
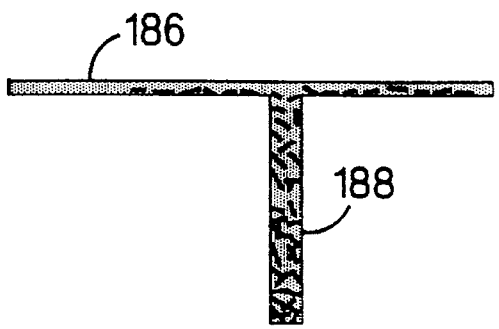
Figure 15B:
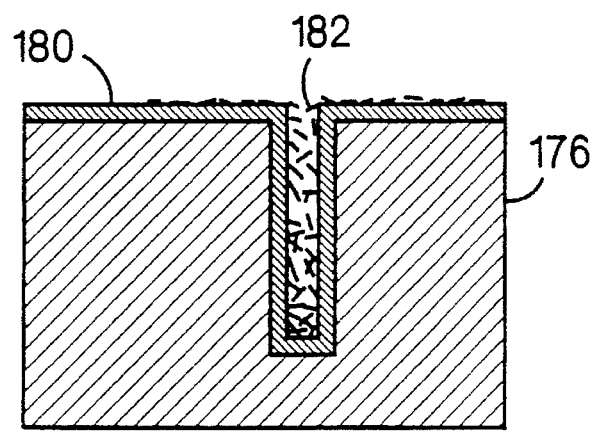

In FIG. 15B, loosely packed tungsten fibers 182 have been applied to the wafer. This is done by spin applying a slurry of tungsten fibers (1 to 10 microns long, 0.1 to 0.5 microns in diameter), in a liquid vehicle of suitable viscosity and volatility such as dodecane or water with surfactants. If desired, the fibers may be cleaned of the horizontal top surface of the wafer and just left in the trenches. Successive spin applications of increasing fiber lengths can be done to create a gradient of decreasing packing density from the bottom to the top of the trench.

Figure 15E:
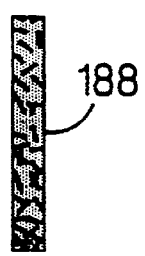
Figure 15C:
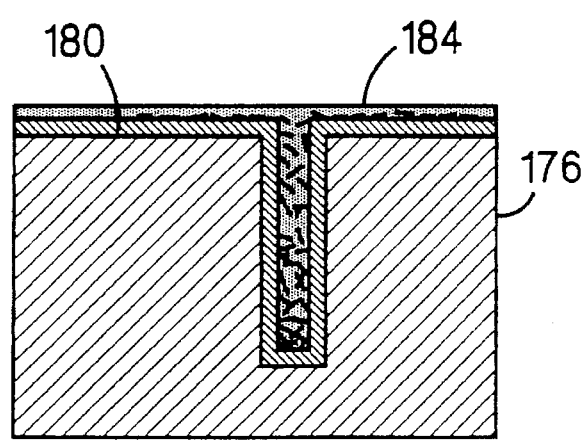

FIG. 15C shows the void space between the fibers filled by CVD polysilicon. Either doped or undoped polysilicon may be used. Recipes for the polysilicon deposition are given below. The CVD deposition process encases the fibers 182 in polysilicon 184. Some voids may be trapped, but this can be minimized by having the fiber packing density decrease from the bottom of the trench to the top. This way channels to the bottom will not become closed before the bottom is filled. As shown in FIG. 15D, the resulting reinforced polysilicon structure has a planar layer 186 and a vertical layer 188. The planar layer 186 may be patterned or completely polished off. Finally sacrificial layer 180 is etched to free the finished part as shown in FIGS. 15D and 15E.

Figure 16A:
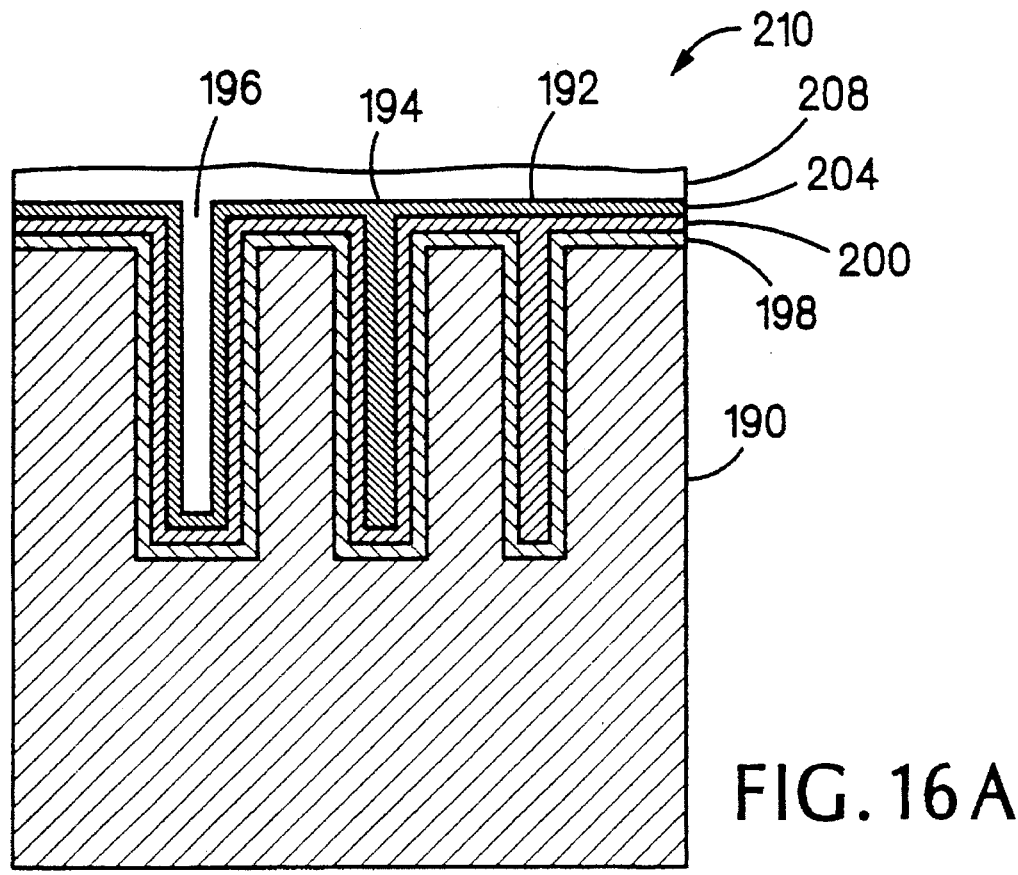
FIGS. 16A and 16B are schematic, cross-sectional views illustrating steps in the fabrication of a multilayer HARMEMS structure.
Figure 16B:
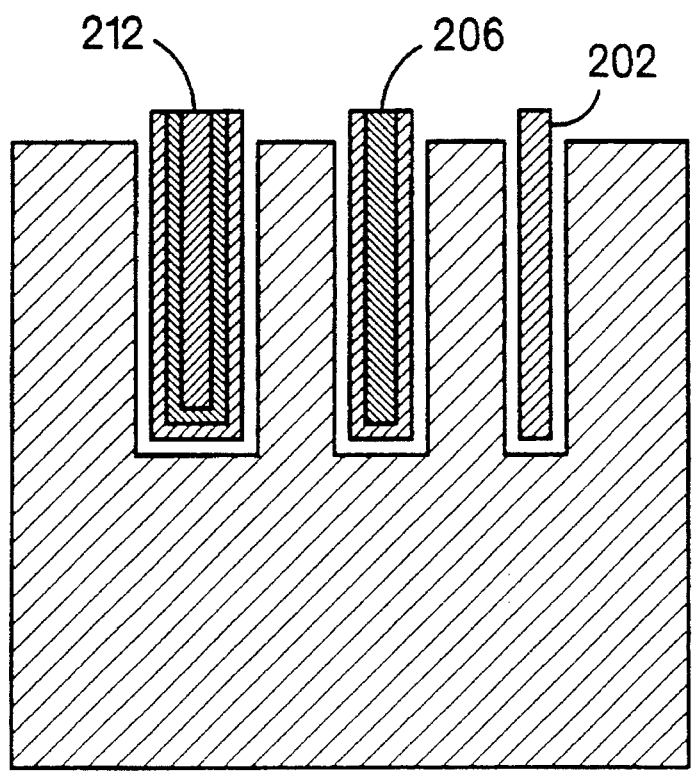

The electrical properties of vertical beams may be controlled by means of varying the trench width, as shown in FIGS. 16A and 16B. FIG. 16A shows a cross-sectional view of a silicon wafer 190 with trenches 192, 194 and 196 etched in it. These trenches have different widths. The surface of the mold wafer 190 has been coated with a sacrificial layer 198 such as silicon dioxide, as discussed above. Sacrificial layer 198 has been coated with a structural layer 200 such as undoped CVD polysilicon which is not electrically conductive. Undoped CVD polysilicon may be deposited at a temperature of 580° C., pressure of 300 mT and silane flow rate of 100 sccm, resulting in a deposition rate of 1 micron in 3 hours. After every 3 microns of deposition and at the end of the deposition, the film should be annealed for one hour in nitrogen at a temperature of 1000° C., followed by native oxide removal with aqueous HF.

At this point the narrowest trench 192 is filled and cannot accept material from subsequent deposition. Thus the beam 202 (FIG. 16B) molded in trench 192 will be insulating, there not being any conductive material in the beam.

Structural layer 204 (FIG. 16A) is deposited next. This layer may be, for example, phosphorus doped CVD polysilicon which is electrically conductive but more resistive than a metal. This deposition may be carried out at a temperature of 610° C., pressure of 375 mT, silane flow rate of 100 sccm and phosphine flow rate of 1 sccm, resulting in a deposition rate of 2 microns in 12 hours. As described for undoped polysilicon, after every 3 microns of deposition and at the end of the deposition, the film should be annealed for one hour in nitrogen at a temperature of 1000° C., followed by native oxide removal with aqueous HF.

Now the second trench 194 is full. Thus the beam 206 (FIG. 16B) molded in trench 194 will be resistive.

The next layer of material 208 may now be deposited to fill the widest trench 196. Layer 208 may be a metal such as electroless plated nickel, which may be deposited using a commercially available plating kit from Buehler Inc., 41 Waukegan Rd., Lake Bluff, Ill. 60044. Magnetic materials may also be plated such as electroless cobalt phosphorus. Electroplating is possible if a seed layer (for example 100 angstroms of sputtered copper) is first applied. This enables microfabricated embodiments of many types of magnetic actuators, sensors and transducers. Thus beam 212 molded in trench 196 may be a conductor or magnetic element.

The planar layer 210 of deposited material may be patterned, or it may simply be ground off to leave only the vertical beams 202, 206 and 212 formed in trenches 192, 194 and 196. FIG. 16B shows the wafer after the sacrificial oxide 198 has been etched with 49% aqueous HF and the beams are ready to be removed from the mold.

In addition to solid multilayer beams, tubular multilayer beams can also be fabricated. For some applications there may be a preference for either solid or tubular beams depending on the performance requirements. Solid beams have the advantage that only one wafer is needed for the mold. Tubular beams require two wafers for the mold, but have the advantage that much thinner films can be deposited to achieve a given stiffness, thus reducing processing time, and the inner layers are not exposed at the beam surface.

Figure 17B:
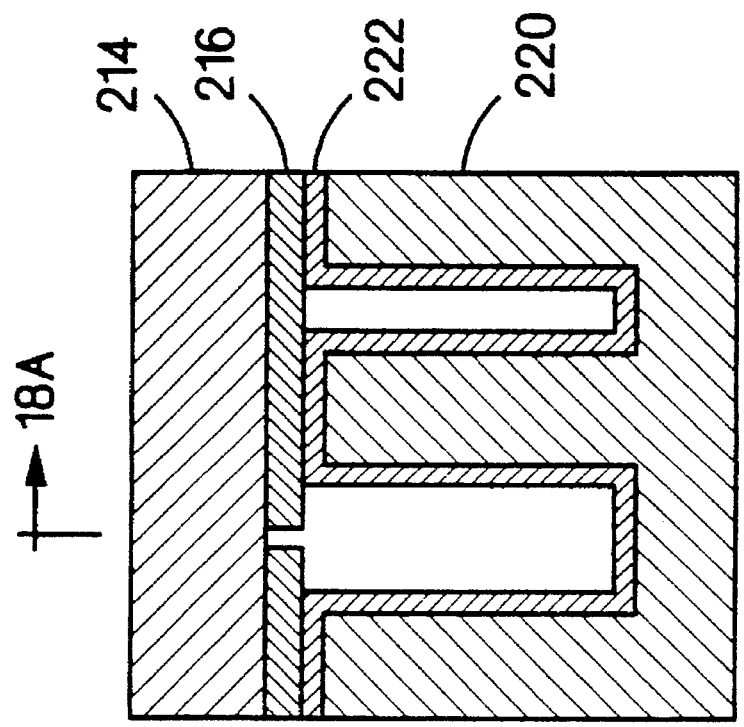
Figure 17A:
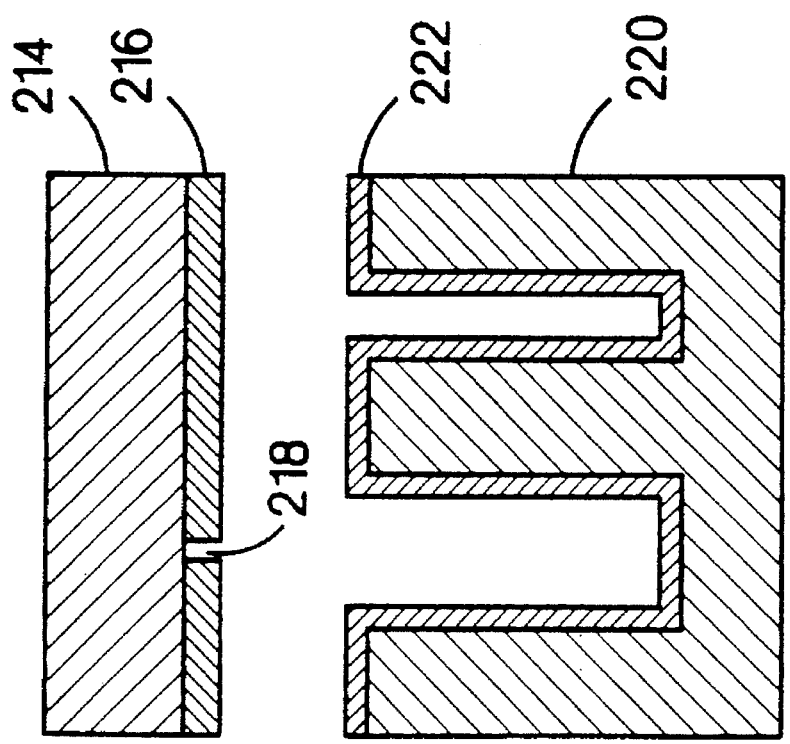
Figure 18A:
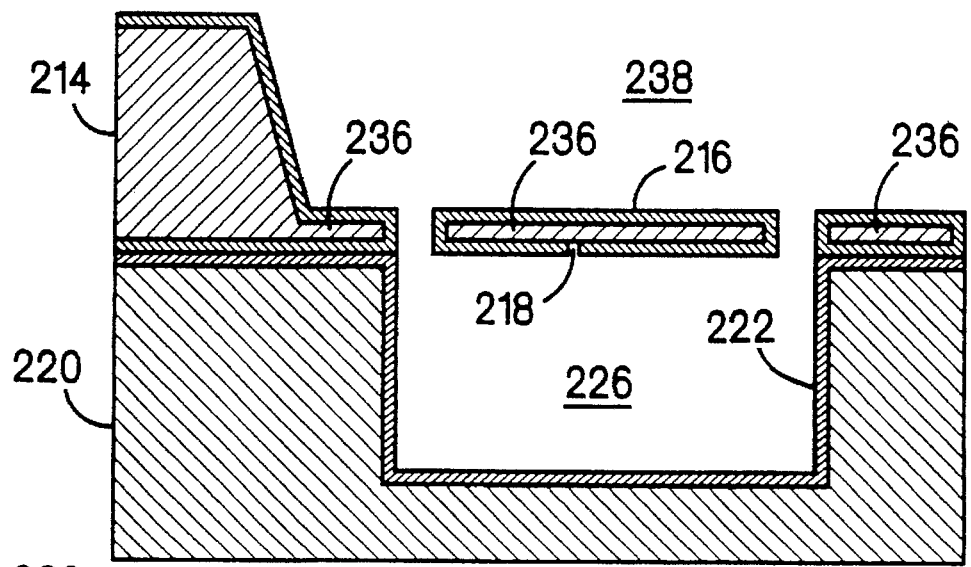
FIG. 18A is a schematic cross-sectional view taken on line 18A-18A of FIG. 17B.

FIGS. 17A–17E and 18A–18C show the process for forming multilayer tubular beams. In FIG. 17A, a wafer 214 with a flat surface has been coated with a sacrificial oxide layer 216. This layer has been patterned with anchor windows 218 where anchor points connecting this wafer to the molded structures will be formed. Anchor windows 218 are the only exposed areas of silicon. Everywhere else the silicon is covered with sacrificial oxide 216. A second silicon wafer 220 has been etched as described above to define the trenches for molding the part. This wafer is also coated with sacrificial oxide 222. The two wafers are bonded together by means such as anodic bonding. Anodic bonding may be carried out for 30 seconds at 500° C. and 1000 volts. Orthogonal cross-sections through the resulting structure are shown in FIGS. 17B and 18A.

Next, a first layer of structural material is deposited in the mold (FIG. 17C). For example, CVD polysilicon 224 may be deposited as described above, to line the surfaces of channels 226 and form anchors 228. The silane gas enters through ports 230 (FIG. 18A). Ports 230 allow the influx of gases or liquids from which the deposited layers are formed. These ports may be plasma etched through a 50 to 100 micron thick membrane 236 of silicon left by anisotropic etching (for example, with aqueous potassium hydroxide) to form pits 238.

Figure 18B:
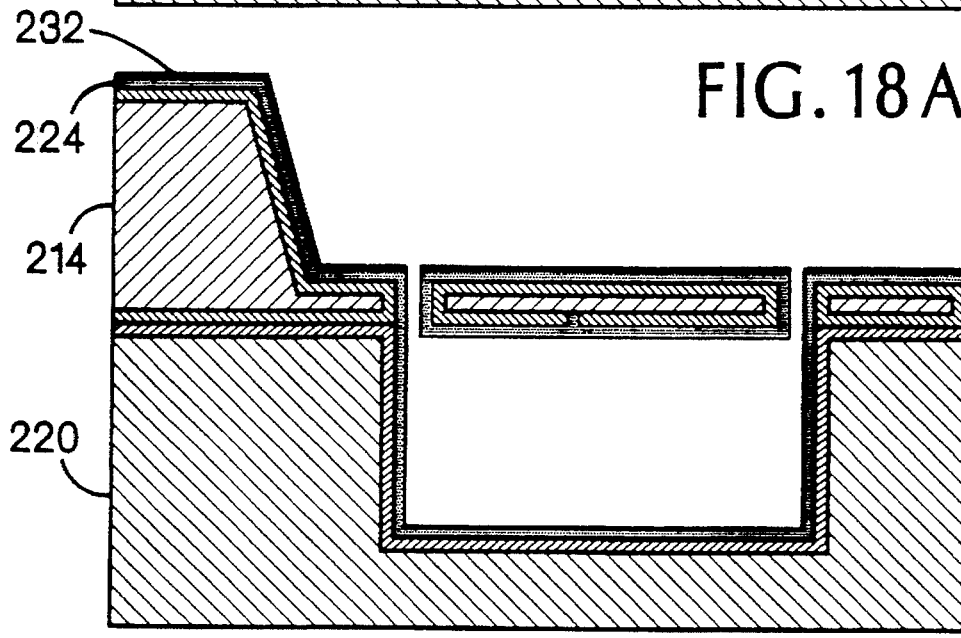
FIG. 18B is a schematic cross-sectional view taken on line 18B-18B of FIG. 17D.

A second layer of structural material 232 may be deposited to coat the inside of the first layer (FIGS. 17D and 18B). If desired, means can be provided, as will be shown later, to confine this deposition to only some of the channels in the mold.

The mold assembly is then plasma-etched to remove layers 224 and 232 from the external surfaces and entryways of the ports 230. This exposes the sacrificial oxide 216 and 222 on wafers 214 and 220.

Figure 18C:
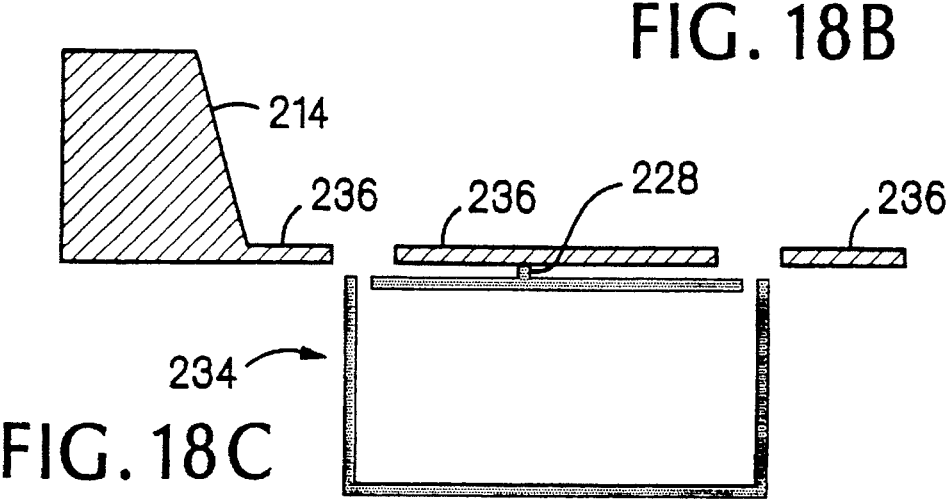
FIG. 18C is a schematic cross-sectional view taken on line 18C-18C of FIG. 17E.
Figure 19:
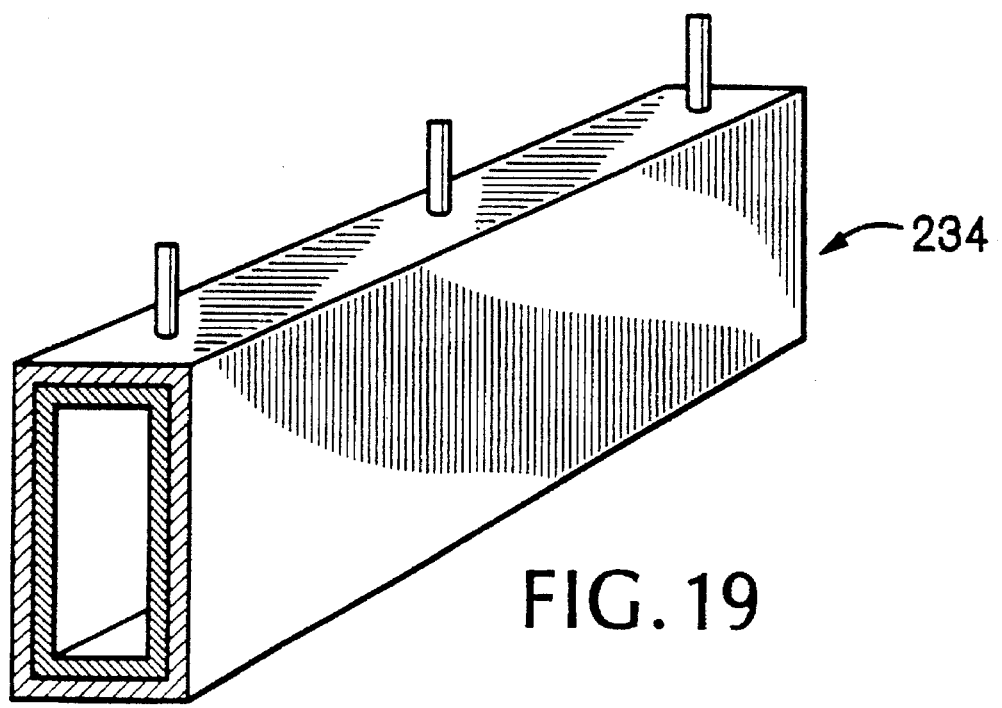
FIG. 19 is a schematic perspective cross-sectional view of a tubular multilayer HARMEMS structure.
Figure 20:
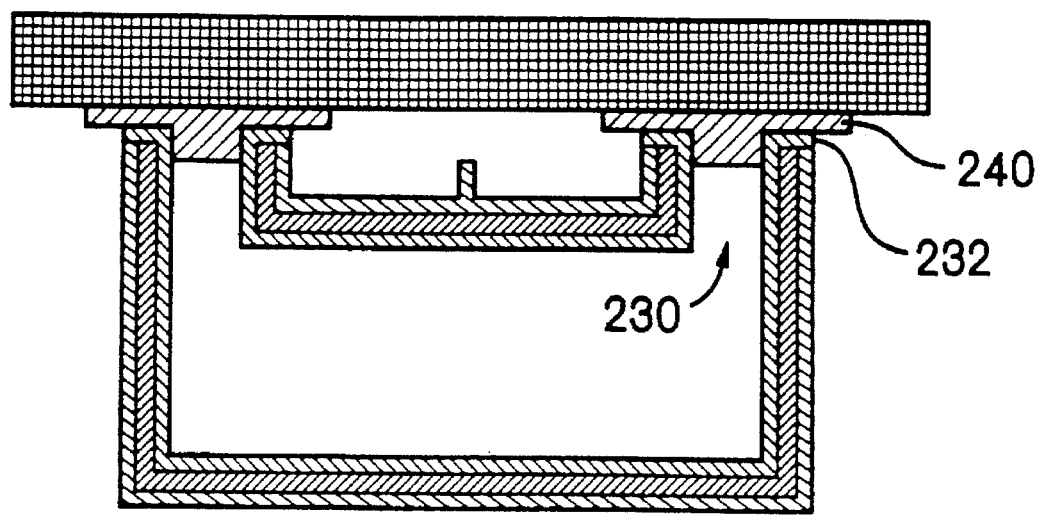
FIG. 20 is a schematic cross-sectional view of electrical contacts to the structure of FIG. 19.

FIGS. 17E and 18C show the finished parts 234 after dissolution of the sacrificial oxide layers 216, 222 by HF, and removal from the lower mold wafer 220. The parts 234 are still held in their as-molded organized relative positions by anchors 228 to the handle wafer 214. They may undergo further processing steps on the handle wafer, or may be removed by mechanically breaking the relatively fragile anchors. The resulting tubular beam is shown in FIG. 19. FIG. 20 shows how electrical contact can be made to the inner layer 232 of the structure through ports 230 using pads of solder paste 240.

Figure 21A:
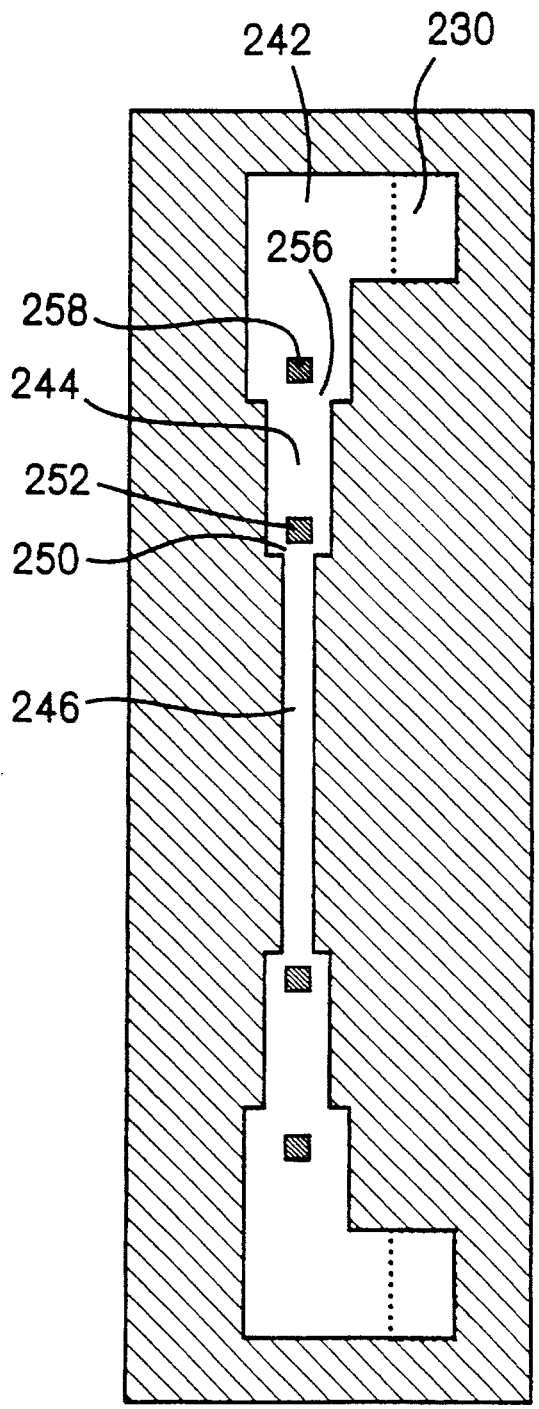
FIGS. 21A and 21B are schematic, cross-sectional views illustrating steps in the fabrication of another tubular multilayer HARMEMS structure.
Figure 21B:
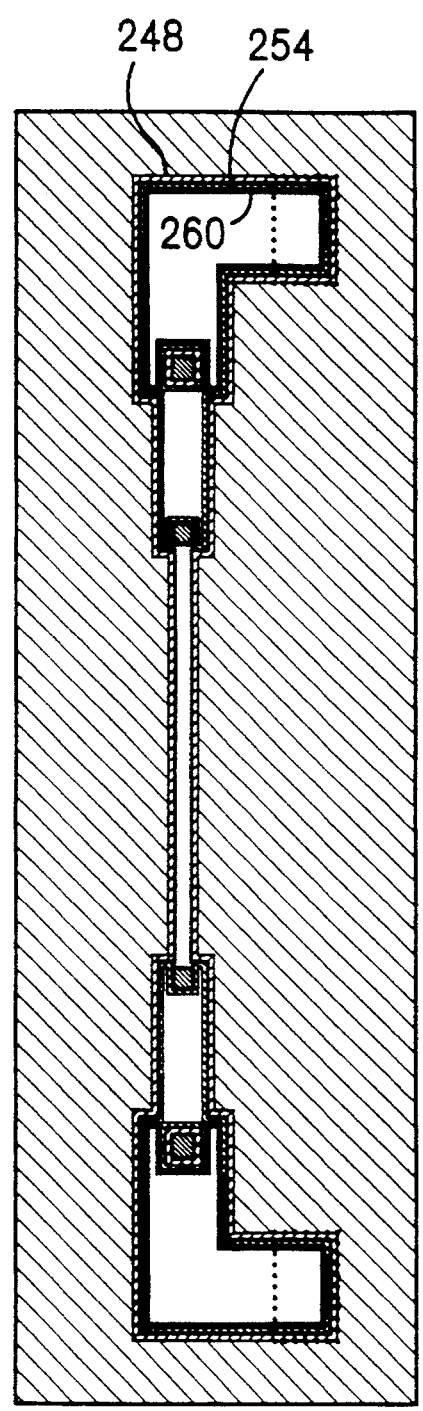

It was mentioned earlier that some of the inner layers may be confined to only certain portions of the tubular beams. The method for fabrication of such beams is shown in FIGS. 21A and 21B. FIG. 21A shows a plan view of a mold cavity with channels 242, 244 and 246 etched in the mold wafer, and ports 230 (shown as dotted outlines) in the overlying handle wafer. Note that the trenches may be of varying width. The entire mold cavity is covered with sacrificial oxide prior to bonding the handle wafer to the mold wafer, as described above. The first layer 248 of structural material (FIG. 21B) lines the entire surface of the mold cavity. Trench section 246 becomes sealed off in this step because the constriction 250 between post 252 and the trench wall is completely filled by material 248. Trench 246 will not receive any more deposited materials from subsequent depositions.

A second deposited layer 254 lines trenches 244 and 242. In so doing, the constriction 256 between post 258 and the trench wall becomes completely blocked by deposited material, thereby isolating trench section 244 from further processing. Isolated trench sections will remain evacuated in the final part. A third structural layer 260 may be deposited in the remaining accessible mold channels 242. The finished part is removed from the mold as described above.

Figure 22:
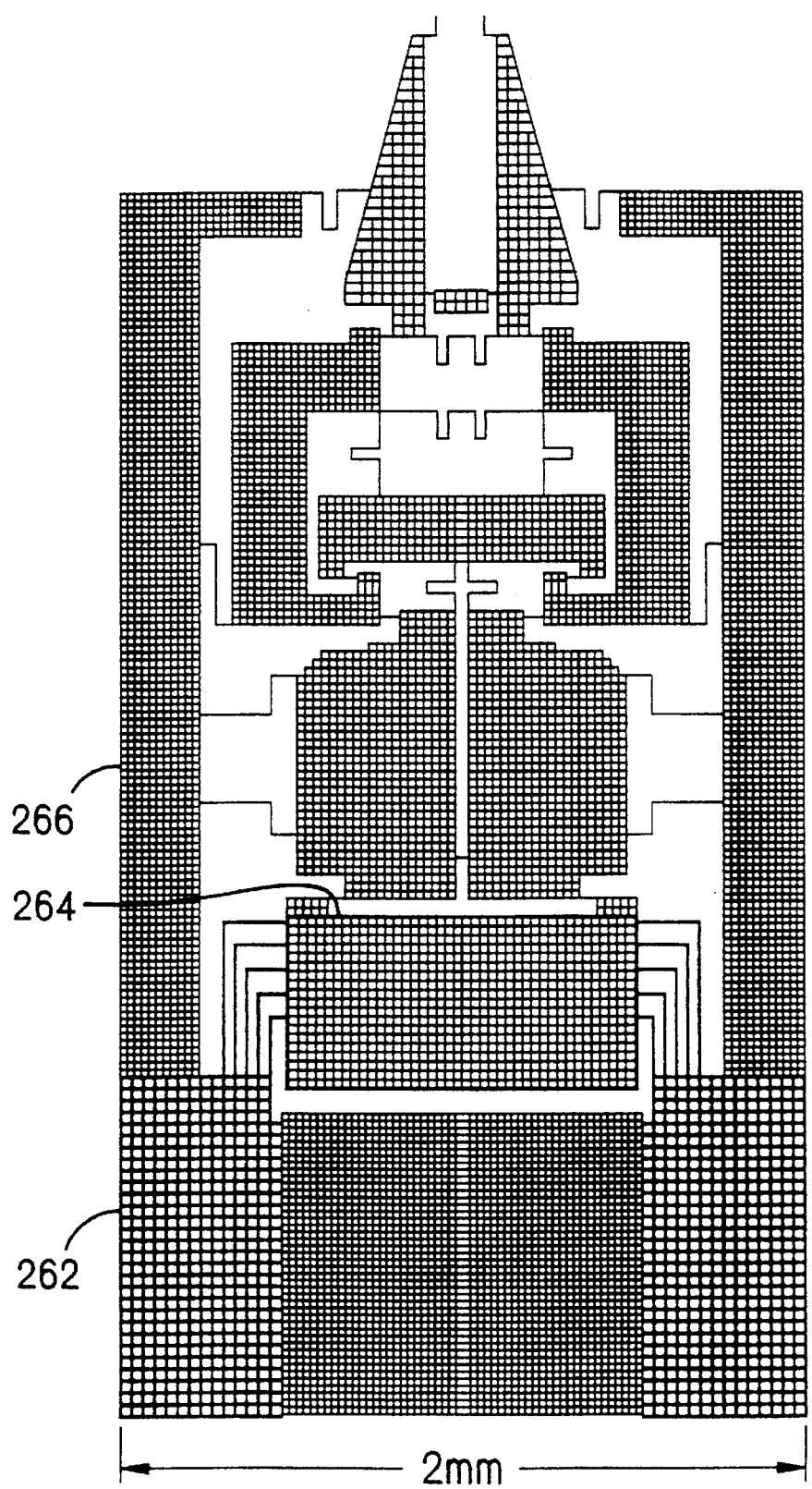
FIG. 22 is a layout of tweezers microfabricated according to the present invention.

The above-described methods for making solid and tubular beams of varying composition can be used to make electronic, mechanical and electromechanical devices such as machines, an example of which are the tweezers whose layout is shown in FIG. 22. In FIG. 22, the widest beams 262 contain nickel so they are good conductors and do not heat up when an electric current is passed through them. They are used as leads to a transducer that operates by dilating as a result of ohmic heating. This transducer is formed out of intermediate width beams 264 which contain doped polysilicon and do not contain nickel so they are moderately conducting and do heat up under the applied current. The narrow beams 266 consist only of undoped polysilicon and are electrically insulating.

Another material property that can vary within a beam is the residual or intrinsic stress. A beam with variable residual stress across its width will bend. Two layer structures or bimorphs can be fabricated that bend either perpendicular to the plane of the mold wafer, allowing fabrication of structures with large vertical dimensions and vertical mold ejection, or in the plane of the wafer, allowing fabrication of structures with smaller clearances than a mold normally allows or biasing of parts against each other.

The fabrication of a bimorph that bends perpendicular to the plane of the mold wafer uses a wide trench that produces a U-shaped beam. The vertical displacement of the beam after release is proportional to the beam width and inversely proportional to the cube of the height of the beam. In the design of the structure, care must be taken to keep the in-plane strain smaller than the mold clearance.

Figure 23A:
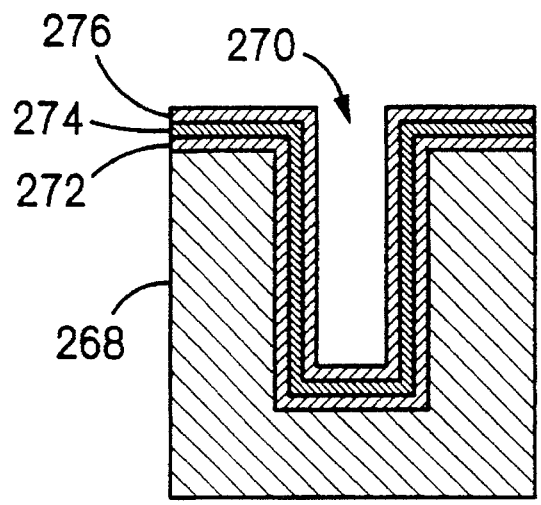
FIGS. 23A-23C, 24A-24E, 25A and 25B are schematic, cross-sectional views illustrating steps in the fabrication of multilayer HARMEMS structures including bimorphs.
Figure 23B:
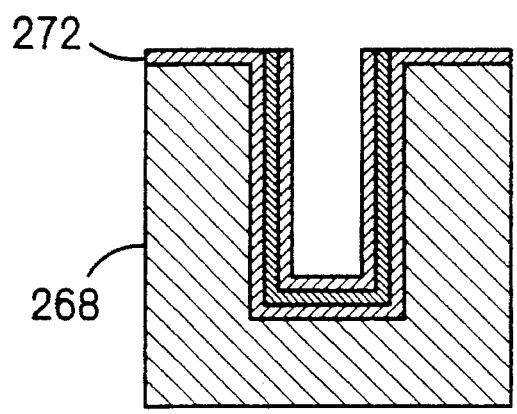
Figure 23C:
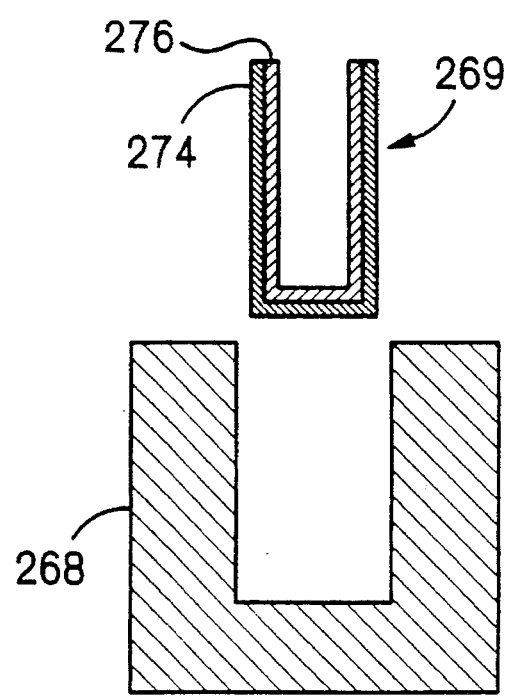

As shown in FIG. 23A, fabrication of such a beam begins with a mold wafer 268 having a trench 270 etched as discussed above. Also as discussed above, the wafer is coated with a sacrificial oxide layer 272. A layer 274 of compressive residual stress polysilicon is next deposited at 620° C. and without annealing. This is followed by the deposition of a stress free layer of polysilicon 276 at 580° C. and with annealing as discussed above. The planar surface layers are then polished off, resulting in the structure of FIG. 23B. As shown in FIG. 23C, the beam 269 is deflected vertically upon etching of the sacrificial oxide layer 272.

Figure 24A:
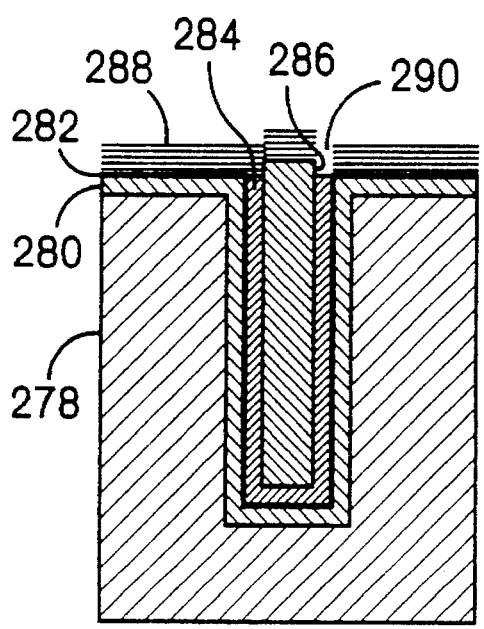
Figure 24B:
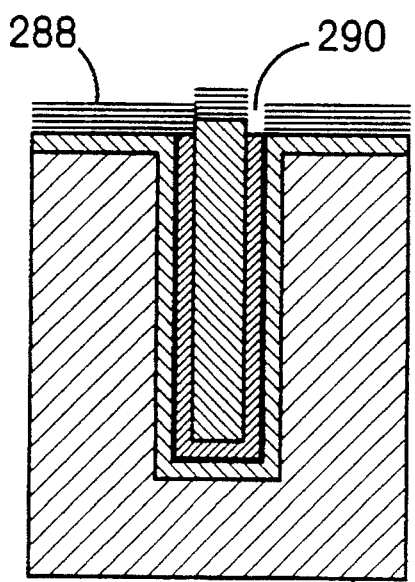
Figure 24C:
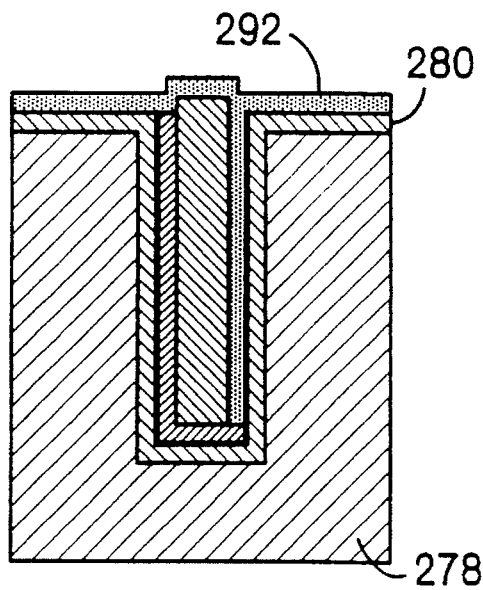
Figure 24D:
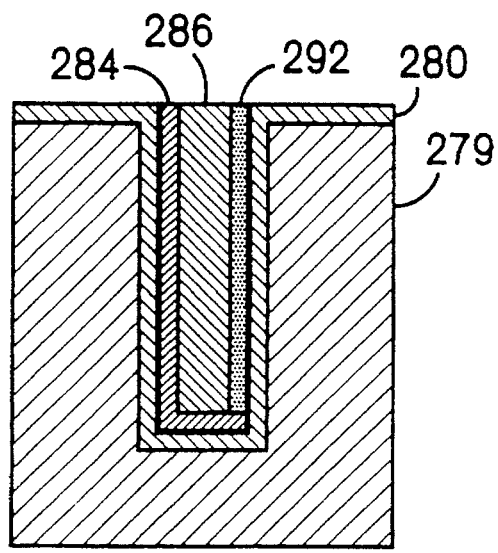
Figure 24E:
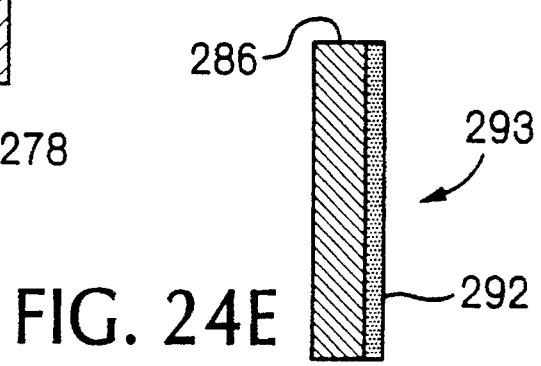

The fabrication of bimorphs with lateral deflection in the plane of the mold wafer is illustrated in FIGS. 24A-24E. Fabrication begins with a mold wafer 278 having a trench etched as discussed above. Also as discussed above, the wafer is coated with a sacrificial oxide layer 280. A layer 282 of low stress silicon rich silicon nitride is next deposited. This deposition may be carried out by CVD at 140 mT and 850° C., with a gas flow of 25 sccm of ammonia and 100 sccm of dichlorosilane, which results in a film growth of 0.25 microns per hour. This is followed by the deposition of a second sacrificial layer of high etch rate phosphosilicate glass (PSG) 284 which was blanket etched to remove the planar layer, and low stress polysilicon 286 which has also been blanket etched to remove the planar layer. Photoresist 288 has been spun over this assembly and patterned to create openings 290 to expose the PSG on one side of the beam where the compressive stress layer is desired. A timed etch with buffered HF (which does not attack photoresist) is done to remove the PSG down to the desired depth in the trench (for example, to the bottom of the trench) as shown in FIG. 24B. Buffered HF may slowly attack the polysilicon, so an alternative is to use plain HF with photosensitive polyimide which can withstand exposure to the unbuffered solution. The thin layer 282 of silicon nitride protects the first layer of sacrificial oxide from contact with HF. The photoresist 288 is next removed, and CVD polysilicon 292 is deposited at the temperature that yields the desired residual stress resulting in the structure of FIG. 24C. The horizontal planar layer may be removed by blanket etch or mechanical polishing resulting in the structure of FIG. 24D. The assembly is put into aqueous HF to remove the sacrificial oxide layers 280 and 284 and the thin silicon nitride 282. The released structure 293 removed from the mold is shown in FIG. 24E. The beam bends laterally when free to do so. Applications for such a bimorph include friction drives, for example for bidirectional stepping actuators for positioning stages; and setting released machines into an operating configuration that is different from the mask layout, such as for electrostatic comb drives wherein one set of comb fingers provides the mold for the second set of interdigitating fingers.

Figure 25A:
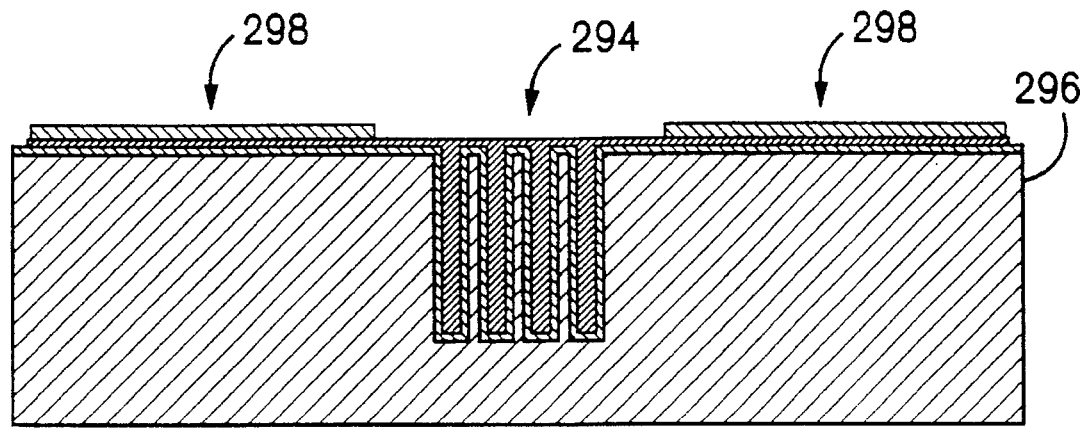
Figure 25B:
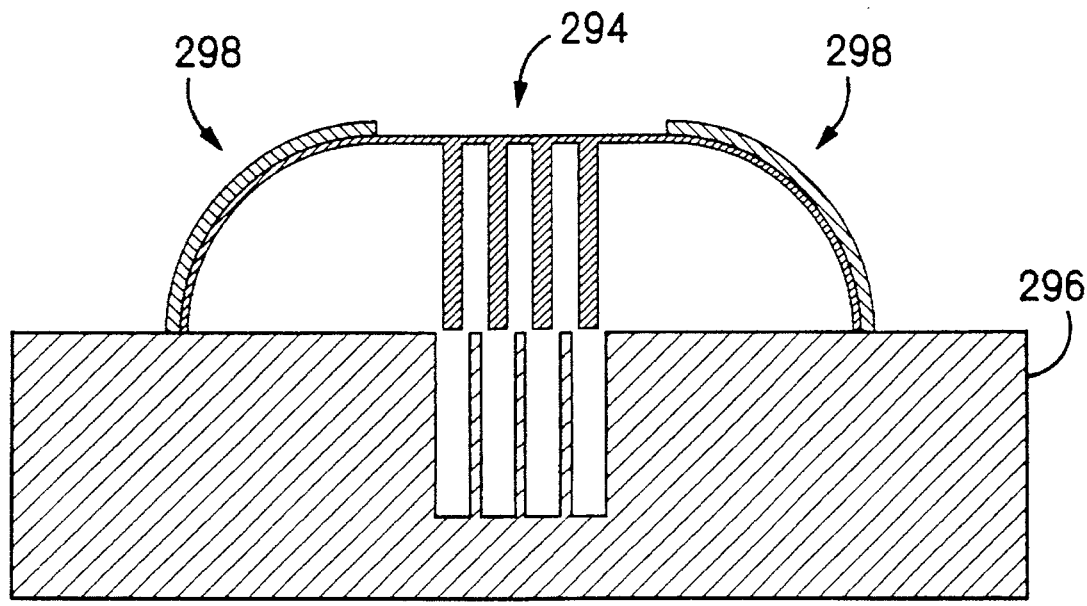

Surface bimorph lifters can be used to lift HARMEMS structures out of their mold as shown in FIGS. 25A and 25B. FIG. 25A shows a HARMEMS structure 294 in its mold 296 prior to the etching of the sacrificial layer. On the top surface of the sacrificial layer and attached to HARMEMS structure 294 are surface bimorph lifters 298. As shown in FIG. 25B, surface bimorph lifters 298 lift HARMEMS structure 294 out of mold 296 when the sacrificial layer is etched. Surface bimorph lifters 298 may be either permanent or sacrificial. Permanent ones may be fabricated using polysilicon as discussed above, and sacrificial ones may be fabricated using tensile silicon nitride and tensile silicon dioxide.

In summary, high vertical aspect ratio thin film structures and methods for their fabrication have been described. Such structures may be used to build fluidic systems and milli-scale micromechanical systems.

The present invention has been described in terms of a preferred embodiment. The invention, however, is not limited to the embodiment depicted and described. Rather, the scope of the invention is defined by the appended claims.

What is claimed is:

1. A method of fabrication of a micromechanical element, comprising:
providing a mold having a depth;
coating said mold with a sacrificial thin film layer;
filling a first portion of said mold with a material having properties;
filling a second portion of said mold with a material having properties at least one of which is different from the material filling said first portion of said mold; and
etching said sacrificial thin film layer.

2. The method of claim 1 wherein said step of providing a mold includes providing a first substrate and anisotropically etching vertical trenches in said first substrate.

3. The method of claim 2 wherein said first substrate is a silicon substrate and said etching of vertical trenches includes coating said first substrate with a masking layer, patterning said masking layer to expose the silicon in the areas where trenches are to be etched, and etching said trenches using plasma etching.

4. The method of claim 3 wherein said step of providing a mold further includes smoothing walls of said trenches by growing thermal oxide on them and etching said thermal oxide away.

5. The method of claim 3 or 4 wherein said step of providing a mold further includes growing a layer of low temperature oxide (LTO) on said mold.

6. The method of claim 2 wherein after said step of coating the mold with a sacrificial layer, a second substrate is provided coated with a sacrificial layer patterned with anchoring holes, and said second substrate is bonded to said first substrate to provide a mold cavity.

7. The method of claim 6 wherein said bonding is anodic bonding or hydrophilic thermal bonding.

8. The method of claim 6 wherein at least one of said first substrate and said second substrate has at least one orifice for providing a mold cavity for a port.

9. The method of claim 1 wherein said step of coating said mold with a sacrificial thin film layer is carried out by chemical vapor deposition.

10. The method of claim 9 wherein said step of coating said mold with a sacrificial thin film layer includes growing a phosphosilicate glass layer.

11. The method of claim 10 wherein said step of coating said mold with a sacrificial thin film layer further includes growing a chemical vapor deposited oxide layer.

12. The method of claim 1 wherein said step of coating said mold with a sacrificial thin film layer includes growing a silicon layer by chemical vapor deposition and oxidizing said silicon layer.

13. The method of claim 1 wherein at least one of said steps of filling a first and a second portion of the mold is carried out by chemical vapor deposition.

14. The method of claim 13 wherein said chemical vapor deposition is chemical vapor deposition of silicon.

15. The method of claim 1 further including a step of reusing said mold.

16. The method of claim 1 wherein said material of said first portion and said material of said second portion have different electrical conductivity.

17. The method of claim 1 wherein said material of said first portion and said material of said second portion have different electronic energy band structure.

18. The method of claim 1 wherein said material of said first portion and said material of said second portion have different residual stress.

19. The method of claim 1 wherein said material of said first portion and said material of said second portion have different dopant concentrations.

20. The method of claim 1 wherein said material of said first portion is a reinforcement for said material of said second portion.

21. The method of claim 1 wherein at least one of said steps of filling a first and a second portion of the mold is carried out by plating.

22. The method of claim 1 further comprising after filling said second portion, filling a third portion of said mold with a material having properties at least one of which is different from the material filling said first portion of said mold, and at least one of which is different from the material filling said second portion of said mold.

23. The method of claim 22 wherein filling said first, second and third portions is carried out by thin film deposition, and no patterning is performed between the filling of the first, second and third portions and the mold has a variable wall-to-wall spacing whereby a micromechanical element with variable controlled material properties is formed.

24. A thin film structure, comprising: a network of members shaped as ribs or tubes having a thickness and wherein an extent of said thin film structure in any direction is greater than about twice said thickness, a first portion of said structure being composed of a material having properties, and a second portion of said structure being composed of material having properties at least one of which is different from the material composing said first portion of said structure.

25. The structure of claim 24 having a lowest extent between about 5 microns and about 250 microns.

26. The structure of claim 24 or 25 wherein said thin film structure has a film thickness between about 5 microns and about 15 microns.

27. The structure of claim 24 wherein said members form substantially rigid portions connected by substantially flexible links.

28. The structure of claim 27 wherein said substantially rigid portions are networks of said members.

29. The structure of claim 28 wherein said networks are honeycomb-shaped.

30. The structure of claim 27 wherein said substantially rigid portions and said substantially flexible links form a machine.

31. The structure of claim 30 wherein said machine is powered by an actuator.

32. The structure of claim 31 wherein said actuator dilates as a result of ohmic heating.

33. The structure of claim 24 wherein said material of said first portion and said material of said second portion have different electrical conductivity.

34. The structure of claim 24 wherein said material of said first portion and said material of said second portion have different electronic energy band structure.

35. The structure of claim 24 wherein said material of said first portion and said material of said second portion have different residual stress.

36. The structure of claim 24 wherein said material of said first portion and said material of said second portion have different dopant concentration.

37. The structure of claim 24 wherein said material of said first portion is a reinforcement for said material of said second portion.

38. The structure of claim 24 wherein a third portion of said structure is composed of a material having properties at least one of which is different from the material of which said first portion of said structure is composed, and at least one of which is different from the material of which said second portion of said structure is composed.

39. A thin film structure, comprising:

a network of members shaped as ribs or tubes having a thickness and a bimorph for lifting said network out of a mold and wherein an extent of said thin film structure in any direction is greater than about twice said thickness.

* * * * *